(12) United States Patent
Eden, III et al.

(10) Patent No.: US 11,278,264 B2
(45) Date of Patent: Mar. 22, 2022

(54) ORAL FLUID, SALIVA AND SPUTUM COLLECTION DEVICE AND METHOD

(71) Applicant: OraSecure LLC, Mogadore, OH (US)

(72) Inventors: Thomas M. Eden, III, West Point, GA (US); Mary E. Hines, Mabank, TX (US); Patricia G. McCoy, Kettering, OH (US); William Corl, Peninsula, OH (US)

(73) Assignee: OraSecure LLC, Mogadore, OH (US)

( * ) Notice: Subject to any disclaimer, the term of this patent is extended or adjusted under 35 U.S.C. 154(b) by 0 days.

(21) Appl. No.: 17/226,980

(22) Filed: Apr. 9, 2021

(65) Prior Publication Data

US 2021/0353268 A1 Nov. 18, 2021

Related U.S. Application Data

(63) Continuation-in-part of application No. PCT/US2020/029209, filed on Apr. 22, 2020.

(51) Int. Cl.
*A61B 10/00* (2006.01)

(52) U.S. Cl.
CPC ...... *A61B 10/0051* (2013.01); *A61B 10/0096* (2013.01); *A61B 2560/04* (2013.01)

(58) Field of Classification Search
CPC ............ A61B 10/0051; A61B 10/0096; A61B 2560/04; A61B 5/14507; B01L 9/06; B01L 2200/026
See application file for complete search history.

(56) References Cited

U.S. PATENT DOCUMENTS 4,589,548 A * 5/1986 Fay .................... A61B 10/0051
206/363
2002/0009389 A1 1/2002 Lappe et al.
(Continued)

FOREIGN PATENT DOCUMENTS

CN 204971357 U * 1/2016
CN 204971357 U 1/2016

OTHER PUBLICATIONS

International Search Report and Written Opinion in International Application No. PCT/US2020/029209, dated Jul. 6, 2020 (11 pages).

*Primary Examiner* — Patrick Fernandes
(74) *Attorney, Agent, or Firm* — Benesch, Friedlander, Coplan & Aronoff, LLP

(57) ABSTRACT

Disclosed herein are devices and methods for collecting oral fluids, saliva, or sputum. One exemplary device includes a collection cup with a hollow needle extending from a bottom end of the cup, where the hollow needle is covered with a compressible sleeve. A clear vacuum tube is positioned beneath the hollow needle. Oral fluids, saliva, or sputum from a donor are collected into the collection cup, and the vacuum tube is pushed onto the hollow needle and the hollow needle passes through the compressible sleeve, through a seal of the vacuum tube, and into the vacuum tube. Oral fluids, saliva, or sputum from the collection cup are drawn into the vacuum tube until the vacuum in the vacuum tube dissipates. An oral fluid specimen is, thus, provided ready for laboratory transport, point of collection screening, or diagnostic analysis while the oral fluid specimen is still in the transparent vacuum tube.

25 Claims, 30 Drawing Sheets

(56) References Cited

U.S. PATENT DOCUMENTS

| | | | |
|---|---|---|---|
| 2004/0005246 A1* | 1/2004 | Efthimiadis | B01L 3/563 422/534 |
| 2005/0010189 A1* | 1/2005 | Toomey | A61B 5/150038 604/403 |
| 2005/0043650 A1 | 2/2005 | Sarstedt | |
| 2014/0073990 A1* | 3/2014 | Holmes | A61B 5/15142 600/575 |
| 2014/0155782 A1* | 6/2014 | Bullington | A61B 5/150992 600/575 |
| 2017/0196542 A1* | 7/2017 | Spiteri | A61J 19/02 |
| 2019/0076131 A1* | 3/2019 | Karlsson | A61J 17/001 |
| 2019/0307382 A1 | 10/2019 | Fedoruk et al. | |
| 2020/0022684 A1* | 1/2020 | Sessions | A61B 10/00 |

\* cited by examiner

ORAL FLUID, SALIVA AND SPUTUM COLLECTION DEVICE AND METHOD

CROSS-REFERENCE TO RELATED APPLICATIONS

This application is a continuation-in-part of International Application No. PCT/US2020/029209, titled "Oral Fluid, Saliva & Sputum Collection Device and Method" and filed on Apr. 22, 2020, which claims priority to U.S. Non-provisional patent application Ser. No. 16/842,220, titled "Oral Fluid, Saliva & Sputum Collection Device and Method" and filed on Apr. 7, 2020, which claims priority to U.S. Provisional Patent Application No. 62/928,406 titled "Filtered Neat Oral Fluid Split Specimen Collection Device" and filed on Oct. 31, 2019, the contents of each of these patent applications being incorporated herein by reference in their entirety.

TECHNICAL FIELD

The present disclosure relates to devices for collecting oral fluids, saliva and sputum. Throughout this disclosure such fluids are collectively referred to as "oral fluids" or "specimens." All three of these fluids generated by the human body have long been found useful for determining the health of people and in particular, for the diagnosis of disease, such as severe acute respiratory syndrome coronavirus 2 (also known as SARS-CoV-2 and, commonly referred to as COVID-19), prediction of disease progression, monitoring of therapeutic drug levels and detection of illicit drugs. In particular, the present disclosure relates to an oral fluids collection device wherein the donor can discharge oral fluids directly from the donor's mouth into a container and wherein the oral fluids can be filtered and drawn into removable vacuum tubes, ready for laboratory transport, point of collection screening, testing, or diagnostic analysis while the oral fluid specimen is still in the transparent vacuum tube.

BACKGROUND

Saliva samples are commonly collected by intra-oral sponge absorption and by direct expectoration into a container. An example of intra-oral sponge absorption is disclosed in U.S. Pat. No. 4,580,577, which describes an absorbent mass (collection paddle) that is masticated by the donor until saturated. The mass is placed in a squeezing device to expel saliva into a holding chamber, out of which a test aliquot can be removed. The problem with the currently marketed collection paddle systems is that the absorbent collection paddle is placed in a particular place in the donor's mouth, is subjected to touching by the donor, comes into contact with the interior of the donor's mouth and tongue and any particulates that may remain in the donor's mouth, and collects from one region of the mouth. In addition, the donor has to place a saturated paddle in the transport tube that contains transport buffer. The transport tube may be subject to spillage and leakage during transportation to the laboratory. Some absorbent collection paddle systems may contain a cotton swab with chemicals to help excite the donor's salivary glands. These chemicals and the cotton swabs add more volume to the saliva sample and may contaminate the sample so that it may be unknown how much of the sample is actually oral fluid. In many cases the cotton swab deteriorates or separates from a plastic portion of the paddle, both while in the donor's mouth and otherwise prior to use, and the volume from one collection to the next can vary depending on how much the cotton has deteriorated. The cotton can also trap particulates from the donor's mouth, therefore adding more volume that is not saliva and could be a contaminant. Foaming and bubbling of oral fluid specimens in this process can compromise laboratory testing. Intra-oral sponge absorption does not provide a split specimen collection nor a mixed saliva specimen. The absorbent materials can cause discomfort for the donor, perhaps even precipitating a biological reaction.

The shortcomings of the current intra-oral sponge absorption were addressed by the Department of Health and Human Services' (DHHS) in its "Mandatory Guidelines for Federal Workplace Drug Testing Programs" (published in the Federal Register at 2019-22684, issued on Oct. 25, 2019, and went into effect on Jan. 1, 2020, the "DHHS Regulation"), which is applicable to all federal employees. This DHHS Regulation allowed for the use of neat oral fluid collection devices. The DHHS Regulation defined the term "undiluted (neat) oral fluid" as "an oral fluid specimen to which no other solid or liquid has been added. For example, see Section 2.4: "a collection device that uses a diluted (or other compartment, process, or method that modifies the volume of the testable specimen) must collect at least one (1) mL of undiluted (neat) oral fluid."

Voiding into an open container eliminates the drawbacks of oral absorption methods but may produce a specimen having unwanted particulates from the mouth and the open container can be prone to spillage. What is needed is an open container method that avoids these problems and is able to meet the regulatory requirements for a "neat oral fluid" specimen.

SUMMARY

The present disclosure describes a device for collecting oral fluids, saliva, or sputum. The device has a tubular housing having a top end and a bottom end. A collection cup having a top end and a bottom end is attached to the top end of the tubular housing. The bottom end of the cup has one or more hollow needles or hollow, pointed, sharp tubes extending from the bottom end of the cup into an interior of the top end of the tubular housing. The bottom end of the cup has one or more openings that open into the one or more hollow needles or hollow, pointed, sharp tubes. The hollow needles or hollow, pointed sharp tubes are covered with a penetrable sleeve to prevent unwanted drainage. One or more vacuum tubes are positioned in the housing. The vacuum tubes have a top end with a penetrable seal and a bottom end. When one or more vacuum tubes are pushed towards the top end of the housing the penetrable seals of the vacuum tubes are penetrated by the hollow needles or hollow, pointed, sharp tubes.

A base is attached to the bottom end of the housing. The base has a vacuum tube holder for the vacuum tubes. In one embodiment the base is constructed to screw into and off of the bottom end of the housing. When the base is screwed into the bottom end of the housing the vacuum tubes are moved upward towards the top of the housing, and the hollow needles or hollow, pointed, sharp tubes are pushed through the penetrable seal of the vacuum tubes. In another embodiment, the base is constructed such that the base slides upward relative to the housing. When the base is slid upward into the bottom end of the housing, the vacuum tubes are pushed upward towards the top of the housing, and the hollow needles or hollow, pointed, sharp tubes are pushed through the penetrable seal of the vacuum tubes. The device can include a removeable tab that is positioned to restrict the base from moving upward into the bottom end of the housing. This tab is kept in place during initial shipping and storage of the device and during the initial collection of a specimen. Once the specimen has been deposited into the collection cup, the tab is removed, which facilitates the movement of the base upward relative to the housing.

A filter may be positioned in an interior of the collection cup to filter the oral fluids to remove bubbles, foam, particulates and other undesirable substances. Additionally, a fill control line may be positioned on the collection cup as a guide when a donor is depositing a specimen into the device.

An advantage of the oral fluid, saliva, and sputum collection device is the collection of a specimen ready for laboratory transport, point of collection screening, testing, or diagnostic analysis while the oral fluid specimen is still in the transparent vacuum tube.

Another advantage is a collection of an oral fluid specimen in a transparent vacuum tube which allows for the use of lasers, fluorescence, and all nanotechnology diagnostic and molecular imaging of nanoparticle options currently in existence or which might exist in the future.

Another advantage is an oral fluid collection device that will reduce overall cost of oral fluid drug testing, human factor errors, opportunities for collector error, opportunities for specimen adulteration by the donor, and incidents of specimen leakage in transport.

Another advantage is a collection of an oral fluid specimen that will provide superior drug recovery characteristics for laboratory testing and/or point of collection screening in accordance with DHHS Regulations and in any application where oral fluid testing is conducted.

Another advantage is that the device allows for a self-collection by donors of their oral fluids in their homes, workplaces, physician's offices, clinics, as well as a collector directed or an observed collection, all without ever requiring the collector to come in contact with the oral fluid specimen.

Another advantage is that the device allows for the collection of an oral fluid sample from a donor, where that oral fluid sample is filtered to remove unwanted particulates and other substances and split into two neat specimens useful in testing and analysis. Such undiluted neat split specimens allow for confirmation of analyses (such as a positive or negative diagnosis or results), as a backup specimen in case of an error in testing or inconclusive result, if a donor disputes the results of the initial test, and other such circumstances.

DETAILED DESCRIPTION OF THE DISCLOSURE

While the following description details the preferred embodiments of the present disclosure, it is to be understood that the disclosure is not limited in its application to the details of arrangement of the devices, parts, components, and methods described and illustrated in the accompanying figures, since the disclosure is capable of applying to other embodiment of oral fluid collection devices, parts, components, and methods of practice.

The present disclosure provides a rapid, safe, secure, and simultaneous split specimen collection device, for self-collection (or collector observed collection) of neat filtered saliva, oral fluid, and sputum specimens, which are transported into test tubes ready for prompt diagnostic screening and testing of a virus such as COVID-19, and of any other substances of interest in these specimens. This oral fluid collection device can provide a neat simultaneous split oral fluid specimen in full compliance with the DHHS Regulations. The due process value in regulated workplace testing (including eventually testing under U.S. Department of Transportation rules and regulations) is to allow the donor who disagrees with the result of a test to demand confirmation testing at a second Substance Abuse and Mental Health Services Administration ("SAMHSA") certified laboratory using the untested split sample. Additionally, in a non-regulated testing situation, the split specimen tube can be used for the analysis of other substances of interest, such as DNA, to prove that the specimen was actually the claimed donor's specimen where a self-collection is conducted, or similar to a situation where numerous vacuum blood tubes are simultaneously taken for diagnostic analysis.

Figure 1:
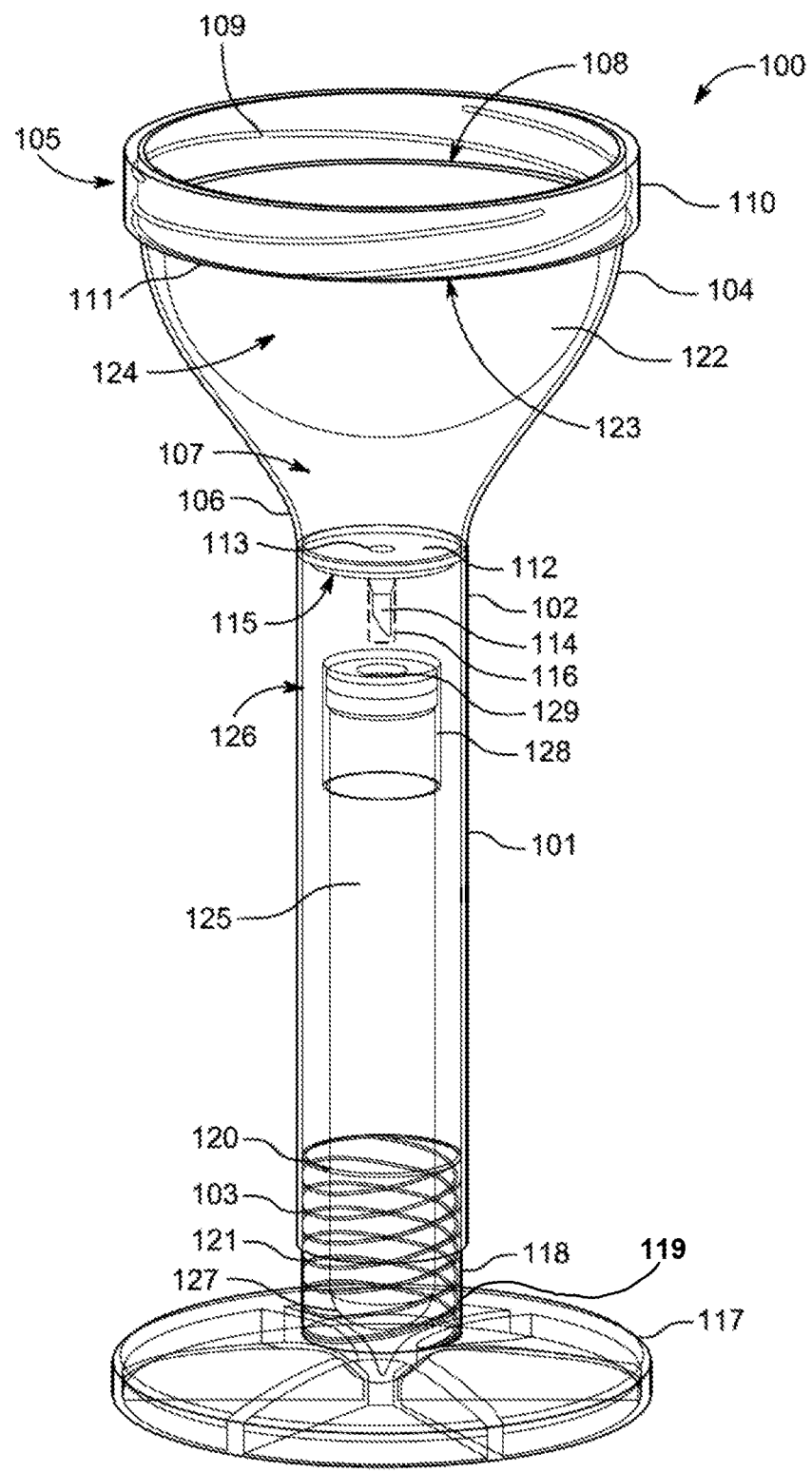
FIG. 1 is a top, side, perspective view of an exemplary embodiment of an oral fluid collection device of the present disclosure.
Figure 2:
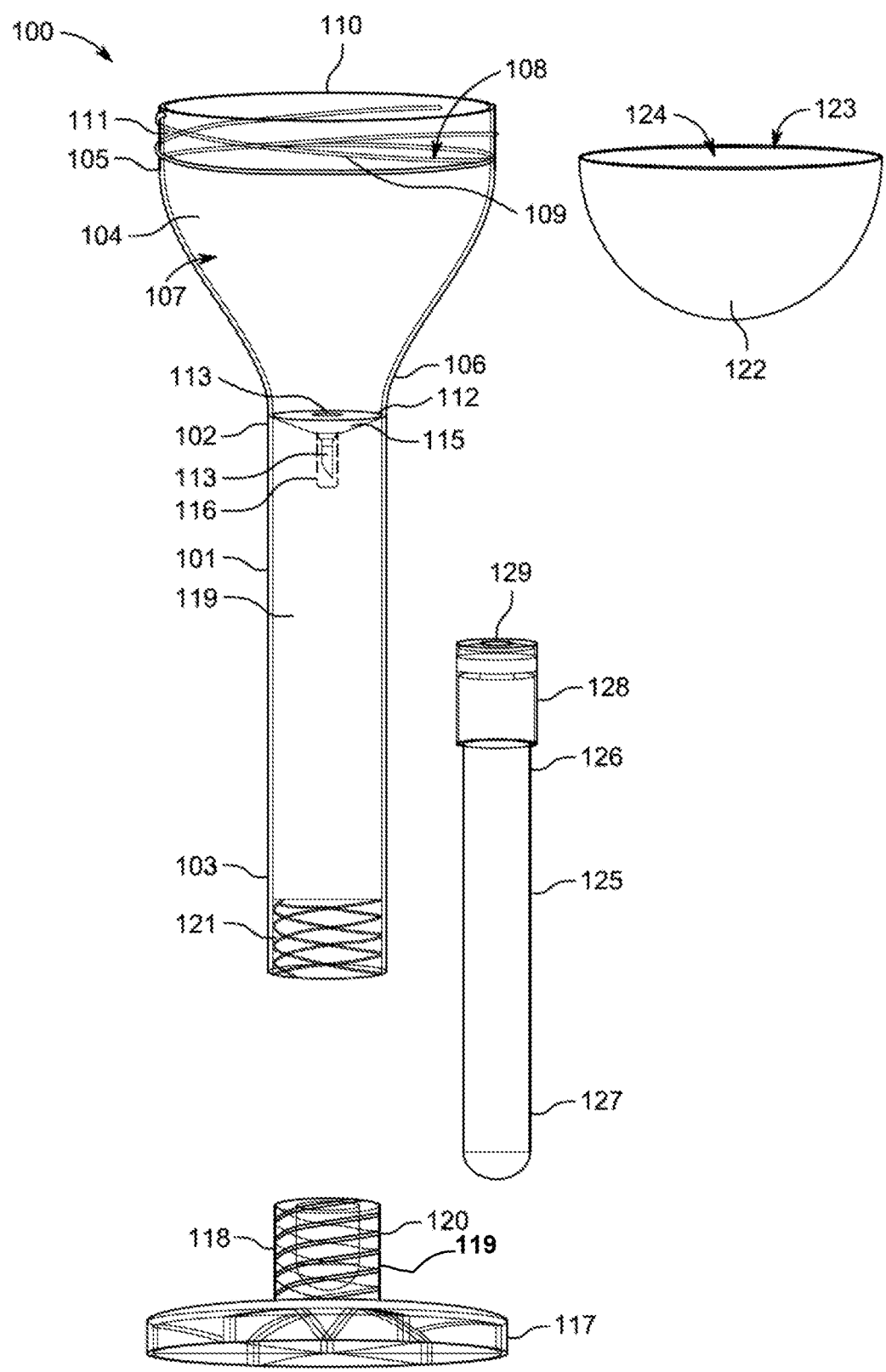
FIG. 2 is an exploded perspective view of the oral fluid collection device of FIG. 1.

FIG. 1 is a top, side, perspective view of an exemplary oral fluid collection device 100 of the present disclosure, and FIG. 2 is an exploded perspective view of the oral fluid collection device. The collection device 100 has a hollow tubular housing 101 with a top end 102 and a bottom end 103 and a collection cup 104 with a top end 105 and a bottom end 106. The collection cup 104 has an interior 107 and an opening 108 at the top end 105 that provides access into the interior 107 of the collection cup 104. The top end 105 of the collection cup 104 has threads 109 around the opening 108 that are arranged to engage a screw-on cap 110 with corresponding threads 111.

The bottom end 106 of the collection cup 104 has an opening 113 for insertion of a hollow needle 114, to facilitate the drainage of liquid through the opening 113 and into the hollow needle 114. The hollow needle 114 extends downward beyond the underside 115 of the bottom end 106 of the collection cup 104 and is covered with a flexible, compressible, penetrable sleeve 116 that prevents unwanted drainage through the hollow needle 114. The hollow needle 114 can take on other arrangements, such as a hollow, pointed, sharp tube; a shard of hollow metal or plastic; or any arrangement that can facilitate the flow of fluids from one location of the other. However for convenience, such components will be referred to as hollow needles throughout this disclosure.

The collection device 100 includes a base 117, where the base 117 includes a stem 119. The base 117 further includes a vacuum tube holder 118 formed by the interior surface of the stem 119 and located generally in the center of the base 117. The bottom end 103 of the housing 101 includes a threaded section 121 along the interior of the housing 101. The exterior of the stem 119 includes corresponding threads 120 for engaging with the threads 121 at the bottom end 103 of the housing 101. The threads 120 of the base 117 can be engaged with the threads 121 of the base 117, and as the threads (120 and 121) engaged and the base 117 is screwed into the housing 101, the vacuum tube holder 118 advances upwards towards the top end 102 of the housing 101. As will be further described, when a vacuum tube 125 is positioned within the vacuum tube holder 118, the vacuum tube 125 will advance upward toward the top end 102 of the housing 101 and toward the hollow needle 114.

The oral fluid collection device 100 has a sieve or filter 122 which has an open end 123 that opens into an interior 124 of the filter 122. The filter 122 is placed inside the interior 107 of the collection cup 104 and, preferably, has a shape which conforms to the shape of the collection cup 104. The open end 123 of the filter 122 is adjacent to the opening 108 of the collection cup 104 at the top end 105 of the collection cup 104. The filter 122 is made of a non-absorbent material such as plastic or metal but paper can also be used. Preferably, the filer is a microfilter. The microfilter is a micro-filtration screen made from a specific weave type, wire diameter, and mesh count for the filtration of suspended solid particles, bubbles and viscous matter in order to provide the ideal fluid specimen. For example, a type 304 stainless steel mesh is used having 0.0098 inch openings with a 0.0037 inch wire diameter. The microfilter is precisely cut and formed to fit the collection cup 104.

A vacuum tube 125 is positioned in the interior of the housing 101. The vacuum tube 125 has a top end 126 and a bottom end 127. The top end 126 is open and has a cap 128 which covers the top end 126. The cap 128 has a flexible penetrable membrane 129 which can be punctured by the hollow needle 114. The compressible sleeve 116 on the hollow needle 114 can also be punctured by the hollow needle 114. Vacuum tubes for collection fluid samples are well known in the art and can be obtained commercially. Flexible, compressive sleeves for the hollow needle 114 can also be obtained commercially.

Figure 3:
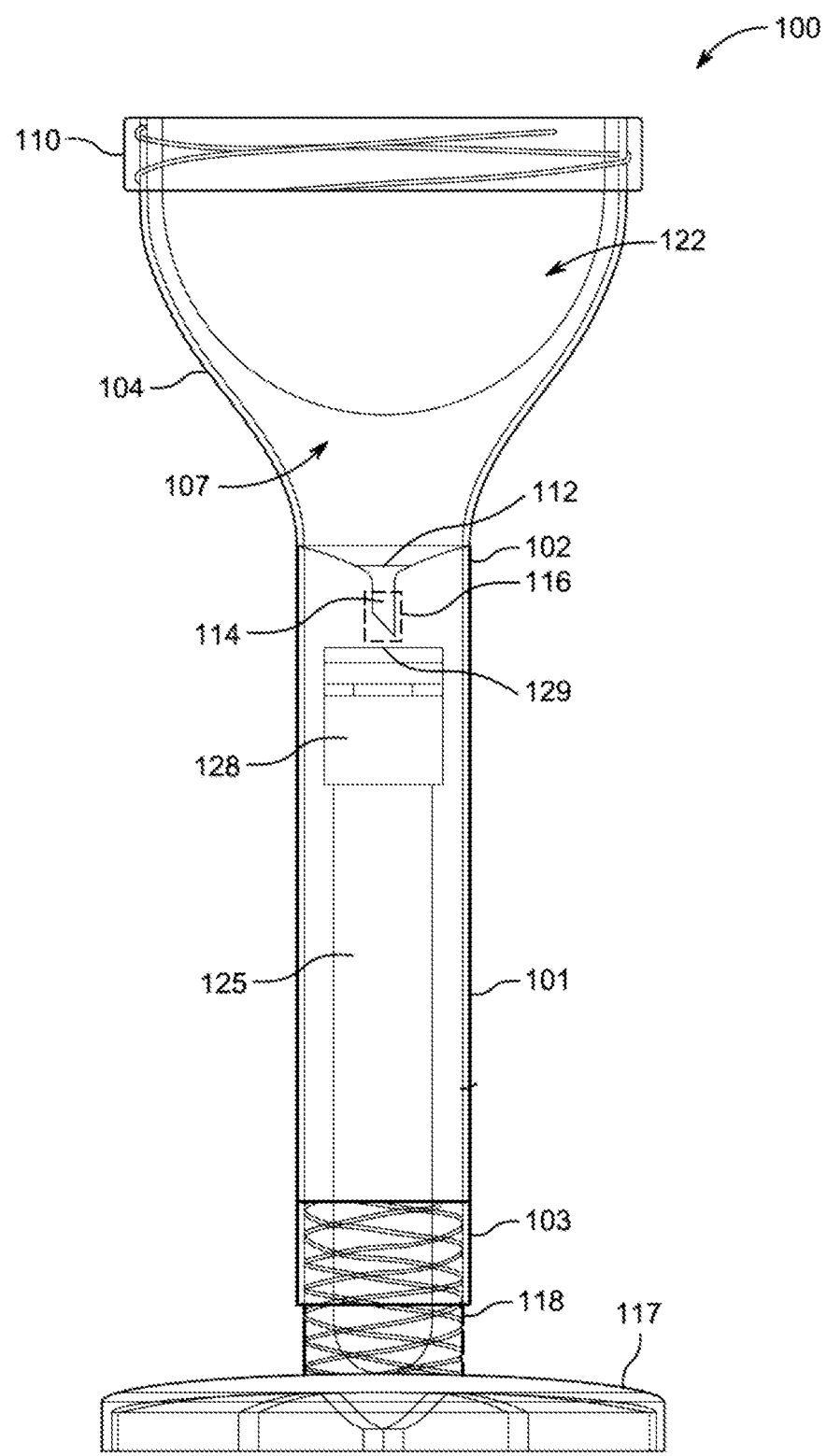
FIG. 3 is a side elevation view of the oral fluid collection device of FIG. 1 in an oral fluid sampling configuration.
Figure 4:
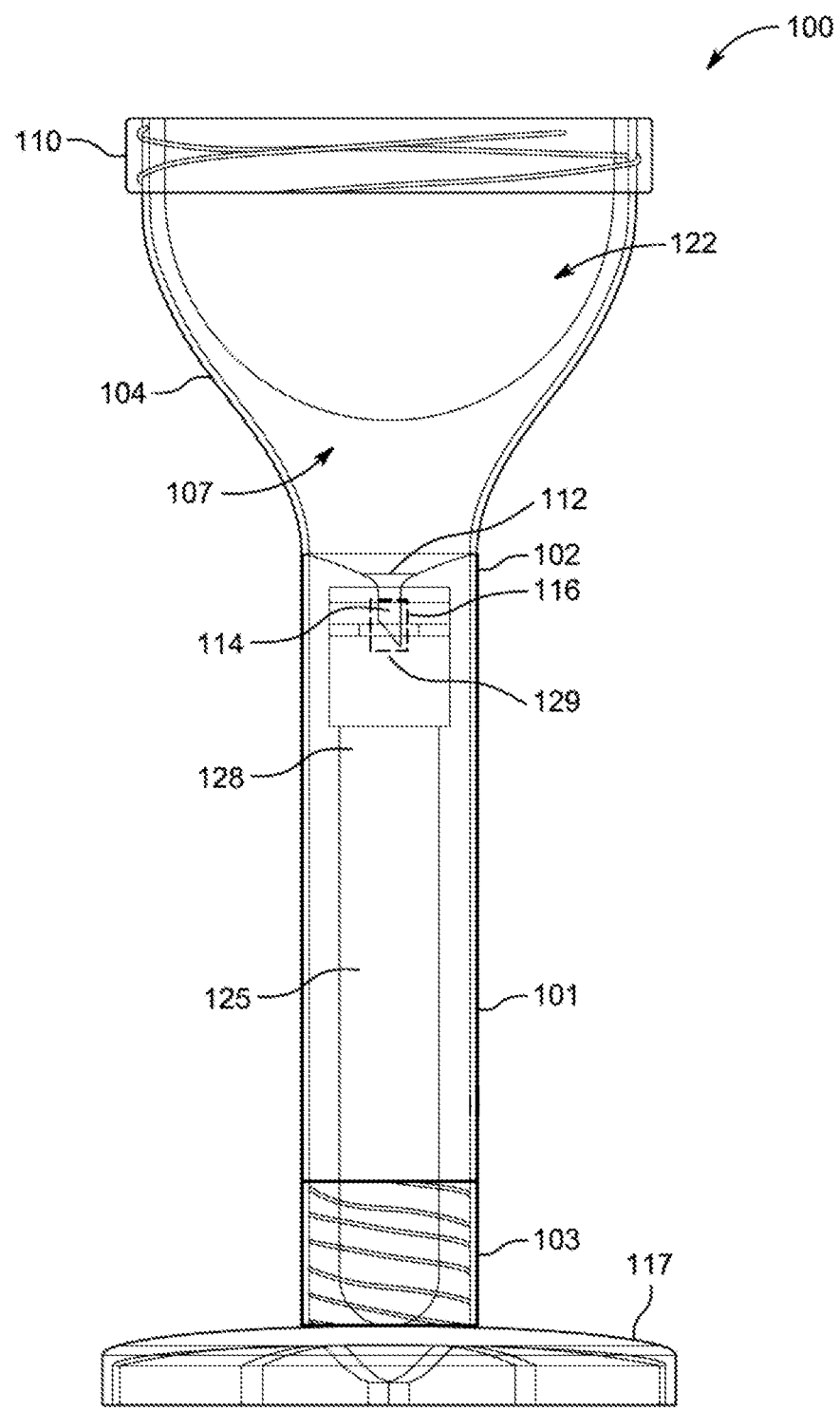
FIG. 4 is a side elevation view of the oral fluid collection device of FIG. 1 in a vacuum tube collection configuration.
Figure 7:
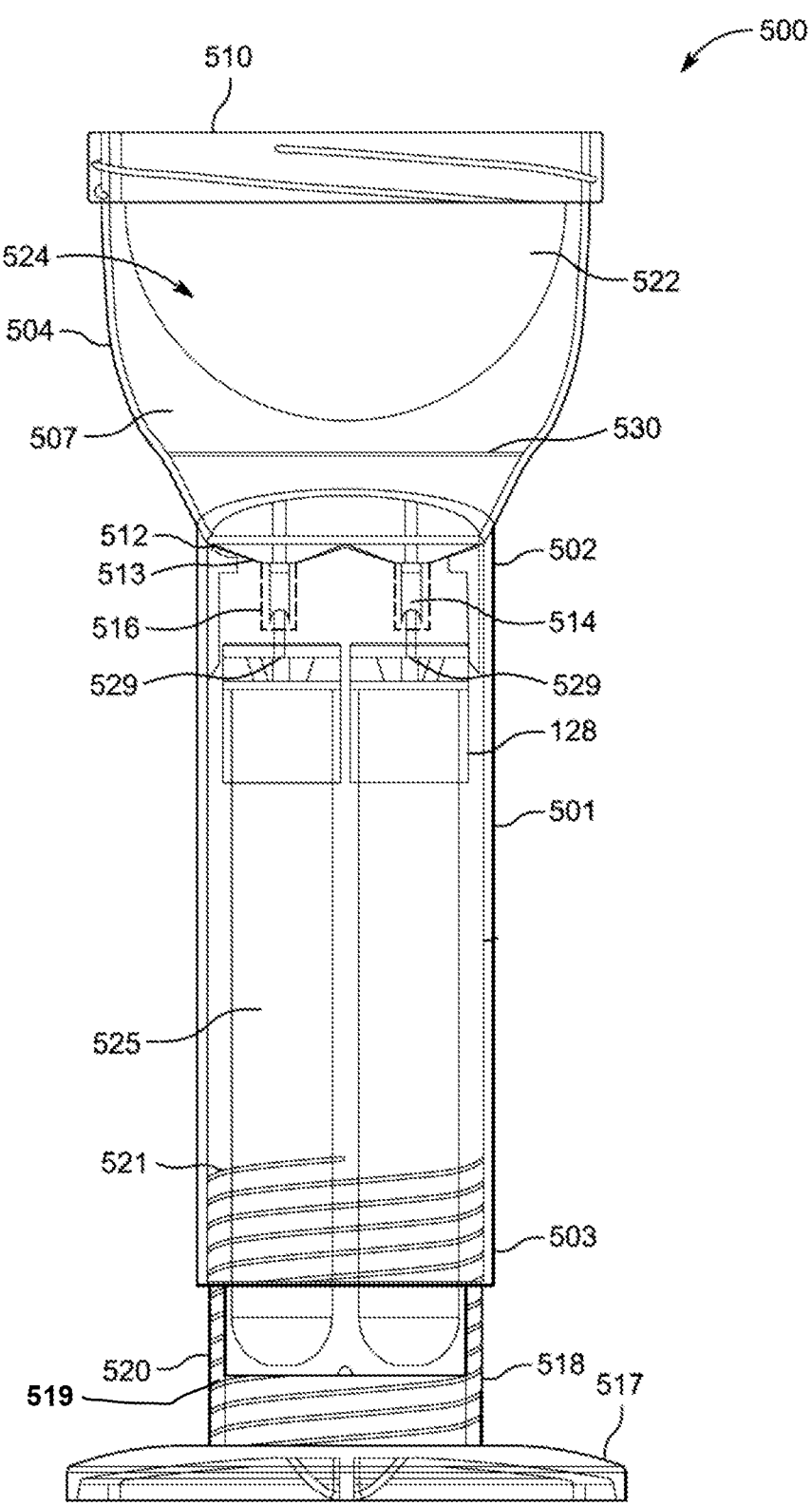
FIG. 7 is a side elevation view of the oral fluid collection device of FIG. 5 in an oral fluid sampling configuration.
Figure 8:
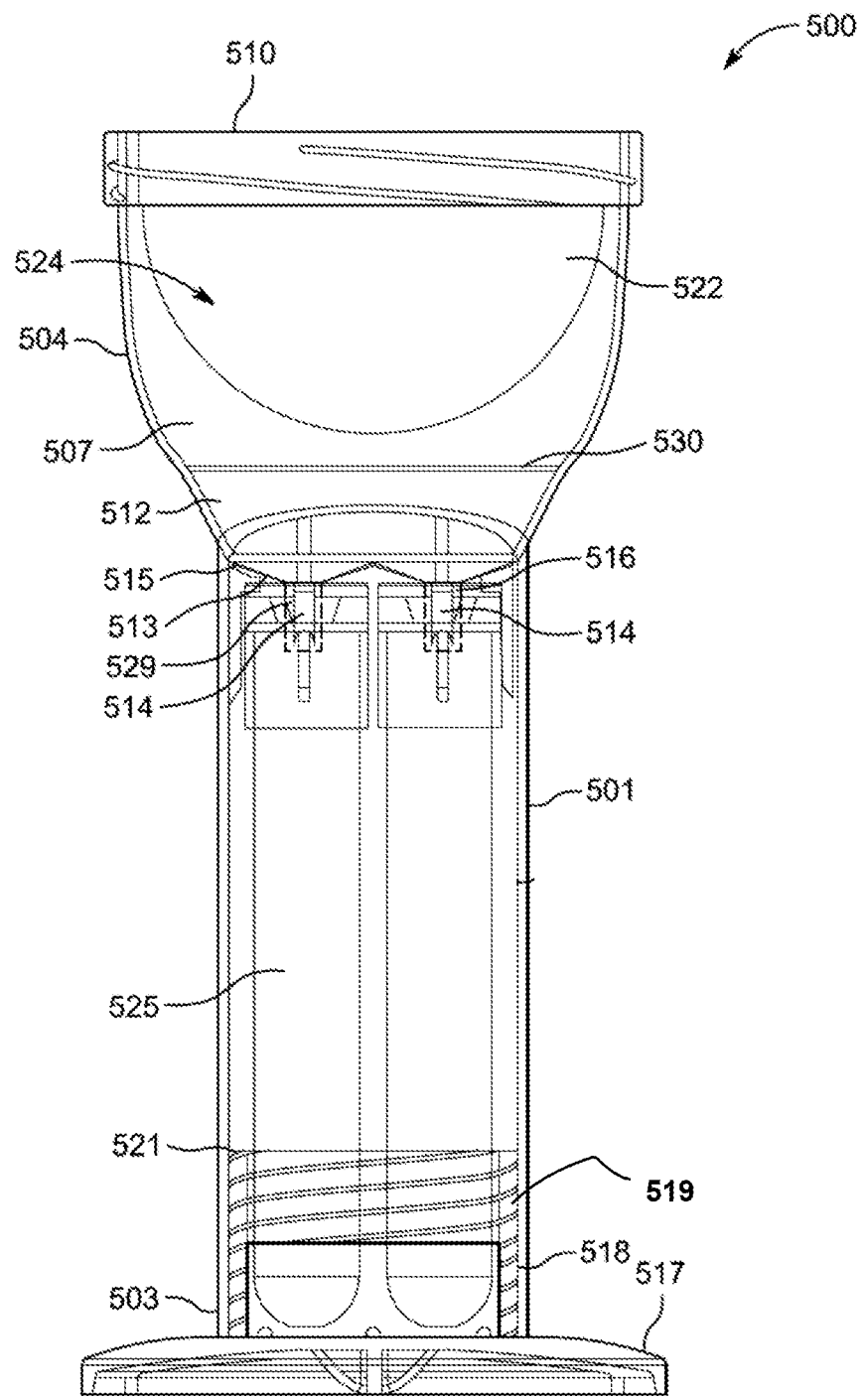
FIG. 8 is a side elevation view of the oral fluid collection device of FIG. 5 in a vacuum tube collection configuration.

FIG. 3 is side elevation view of the oral fluid collection device in an oral fluid sampling configuration. FIG. 4 is side elevation view of the oral fluid collection device in a vacuum tube collection configuration. In use, the cap 110 is unscrewed from the top of the collection cup 104 and a donor voids his or her oral fluids into the filter 122 that is in the collection cup 104. The oral fluids will drain through the anti-foaming filter 122 to the bottom of the collection cup 104 and collect there. The collection cup 104 can have a control fill line (for example, as illustrated in FIGS. 7 and 8 as reference number 530) to guide the donor to provide a sufficient and precise amount of oral fluid. The oral fluid will also drain into the hollow needle 114 but will not flow out of the hollow needle 114 because of the blocking action of the sleeve 116 that is placed over and attached to the hollow needle 114. Sputum can also be collected in this manner but it may be necessary for the donor or the collector to first remove the filter, which can be done manually.

After the oral fluids sample is provided, the cap 110 is replaced on the collection cup 104 and the base 117 of the housing 101 is screwed into the housing 101. As the base 117 is screwed inward, the vacuum tube 125 will move upward and engage the hollow needle 114. As the base 117 is further screwed inward, the cap 128 of the vacuum tube 125 engages the sleeve 116 and the hollow needle 114, and such upward movement results in a force being applied between the hollow needle 114 and the cap 128 of the vacuum tube 125, resulting in the hollow needle 114 penetrating both the sleeve 116 and the membrane 129 in the cap 128 of the vacuum tube 125. The sleeve 116 compress and moves away from the tip of the hollow needle 114, and the vacuum in the vacuum tube 125 pulls the oral fluids into the vacuum tube 125 until the vacuum is dissipated.

Once the vacuum tube 125 is properly filled, the base 117 and the housing 101 are unscrewed, causing the vacuum tube 125 to move downward relative to the housing 101, causing the hollow needle 114 to be removed from the vacuum tube 125. Once the hollow needle 114 is removed, the membrane 129 of the cap 128 of the vacuum tube 125 reseals the vacuum tube 125. The sleeve 116 uncompresses, returns to its original configuration, and again covers the tip of the hollow needle 114. Thus providing users with protection from the sharp portion of the hollow needle 114. The vacuum tube 125 can then be removed from the housing 101 and the vacuum tube holder 118. In one embodiment, the vacuum tube 125 can be held in the vacuum tube holder 118 using a friction fit that is arranged to retain the vacuum tube 125 in the vacuum tube holder 118, while allowing the user to apply a reasonable force to remove the vacuum tube 125 from the vacuum tube holder 118. The vacuum tube 125 containing the sample of oral fluids can then be transferred to a laboratory for analysis.

Figure 5:
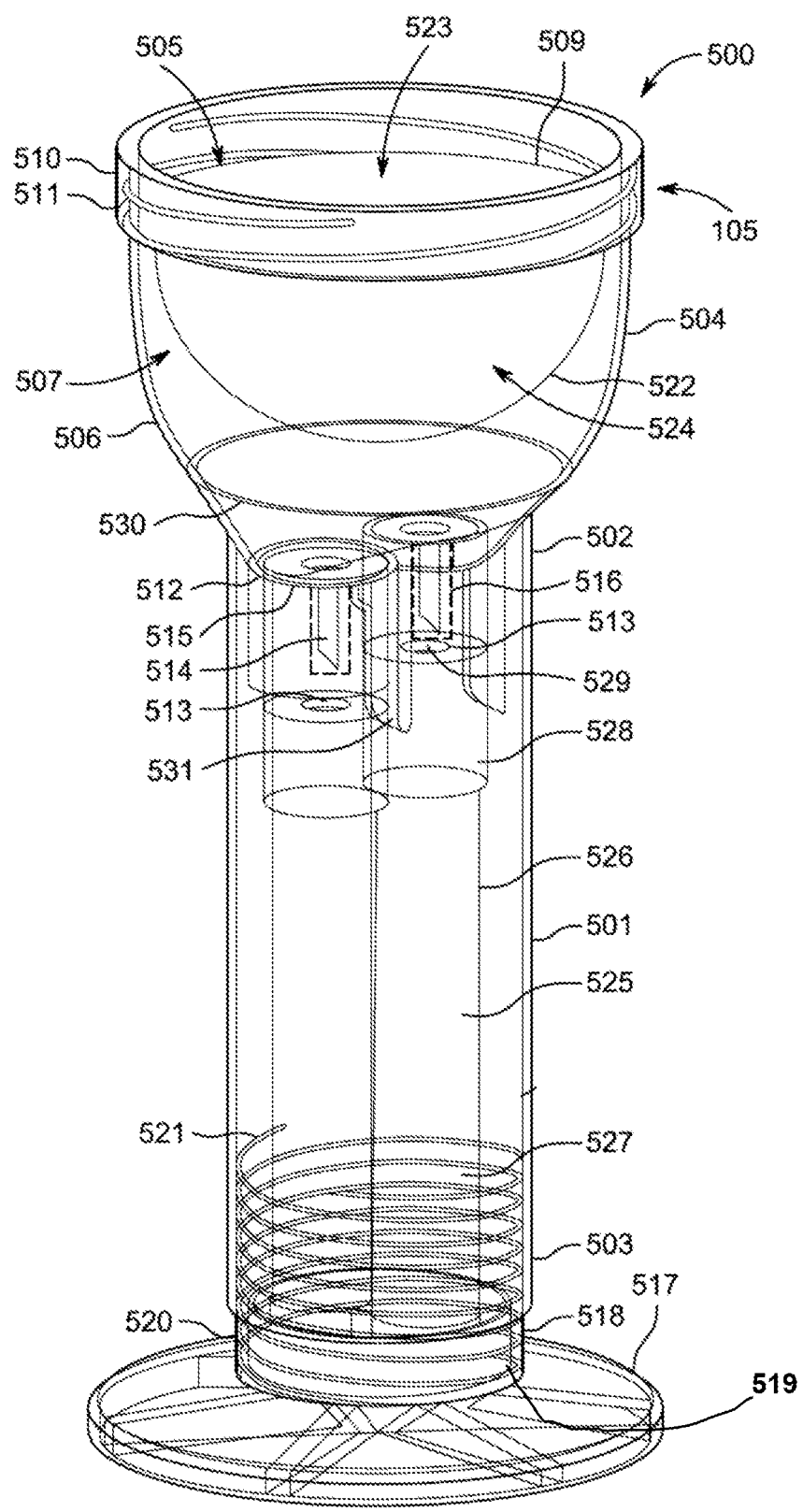
FIG. 5 is a top, side, perspective view of another embodiment of an oral fluid collection device of the present disclosure.
Figure 6:
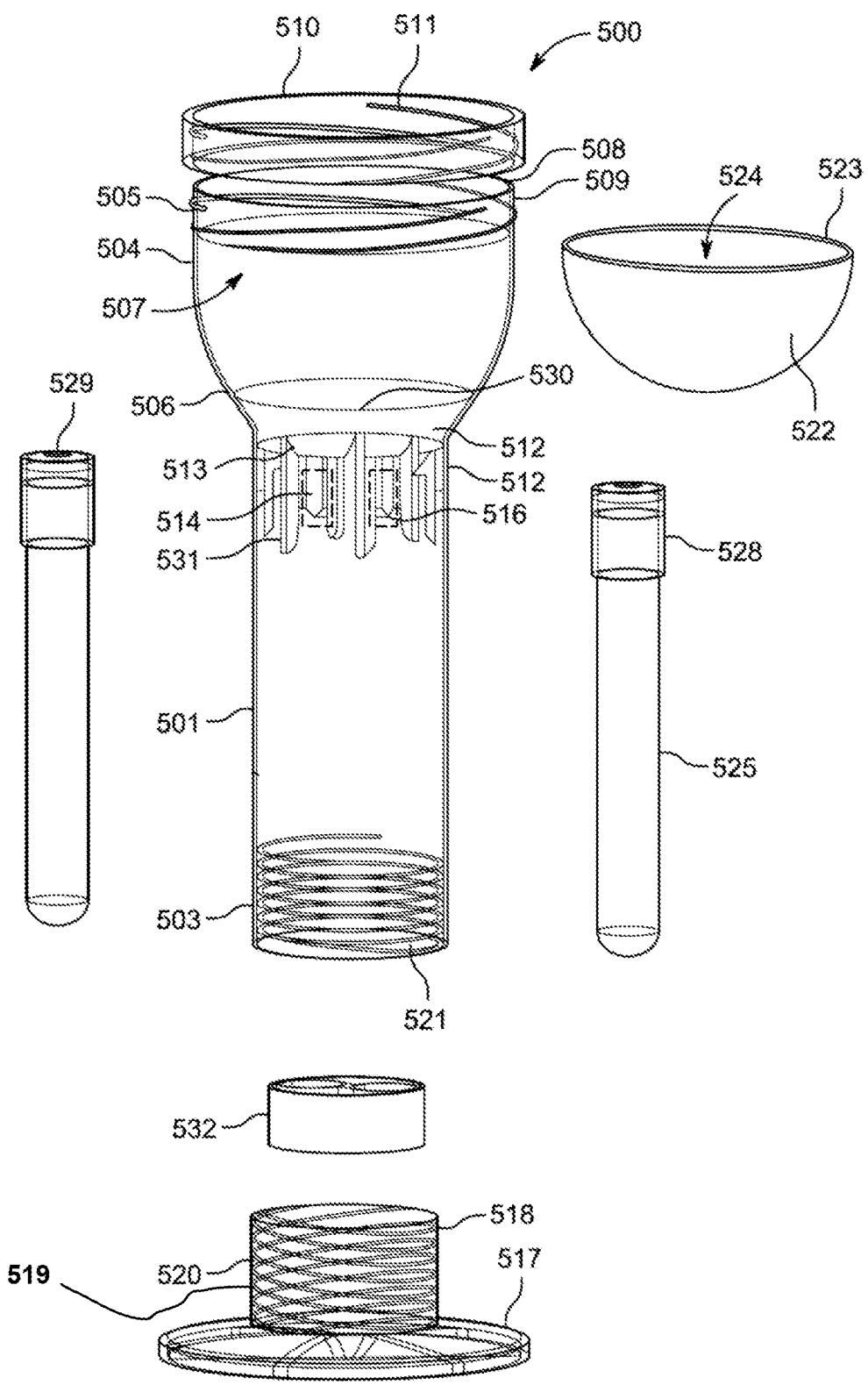
FIG. 6 is an exploded perspective view of the oral fluid collection device of FIG. 5.

In another embodiment, the oral fluid collection device can accommodate a plurality of vacuum tubes. FIG. 5 is a top, side, perspective view of such an embodiment of an oral fluid collection device 500 with two vacuum tubes 525. FIG. 6 is an exploded perspective view of the oral fluid collection device 500 with two vacuum tubes 525. The oral fluid collection device 500 has a hollow tubular housing 501 with a top end 502 and a bottom end 503 and a collection cup 504 with a top end 505 and a bottom end 506. The collection cup 504 has an interior 507 and the top end 505 forms an opening 508 into the interior 507. The top end 505 of the collection cup 504 has threads 509 around the opening 508 engaging a screw-on cap 510 having corresponding threads 511.

The bottom end 506 of the collection cup 504 has an pair of openings 513 for insertion of a pair of hollow needles 514 for drainage of liquid. The hollow needles 514 extend downward beyond the underside 515 of the bottom end 506 and are each covered with a flexible, compressible sleeve 516 that prevents unwanted drainage through the hollow needles 514.

The collection device 500 includes a base 517, where the base 517 includes a stem 519. The base 517 further includes a vacuum tube holder 518 formed by the interior surface of the stem 519 and located generally in the center of the base 517. The bottom end 503 of the housing 501 includes a threaded section 521 along the interior of the housing 501. The exterior of the stem 519 includes corresponding threads 520 for engaging with the threads 521 at the bottom end 503 of the housing 501. The threads 520 of the base 517 can be engaged with the threads 521 of the base 517, and as the threads (520 and 521) are engaged and the base 517 is screwed into the housing 501, the vacuum tube holder 518 advances upwards towards the top end 502 of the housing 501. When a pair of vacuum tubes 525 are positioned within the vacuum tube holder 518, the vacuum tubes 525 will advance upward toward the top end 502 of the housing 501 and toward the hollow needles 514.

The oral fluid collection device 500 has a sieve or filter 522 which has an open end 523 that opens into an interior 524 of the filter 522. The filter 522 is placed inside the interior 507 of the collection cup 504 and, preferably, has a shape which conforms to the shape of the collection cup 504. The open end 523 of the filter 522 is adjacent to the opening 508 of the collection cup 504 at the top end 505 of the collection cup 504.

Vacuum tubes 525 are positioned in the interior 519 of the housing 501. Each vacuum tube 525 has a top end 526 and a bottom end 527. The top end 526 is open and has a cap 528 which covers the top end 525. The cap 528 has a flexible membrane 529, which can be punctured by the hollow needle 514. The compressible sleeve 516 on the hollow needle 514 can also be punctured by the hollow needles 514.

A fill control line 530 is located on the cup 504, vacuum tube guides 531 are positioned at the bottom 512 of the collection cup 504, and a vacuum tube tray 532 is shown for insertion into the vacuum tube holder 518. The vacuum tube guides 531 and the vacuum tube tray 532 prevent the vacuum tubes 525 from rotating as the base 517 is screwed into and off of the bottom end 503 of the housing 501. The vacuum tubes 525 may also have control fill lines to verify accuracy.

FIG. 7 is side elevation view of the oral fluid collection device 500 in an oral fluid sampling configuration. FIG. 8 is side elevation view of the oral fluid collection device 500 in a vacuum tube collection configuration. The oral fluid collection device 500 is used in a similar manner as described for the oral fluid collection device 100.

Figure 9:
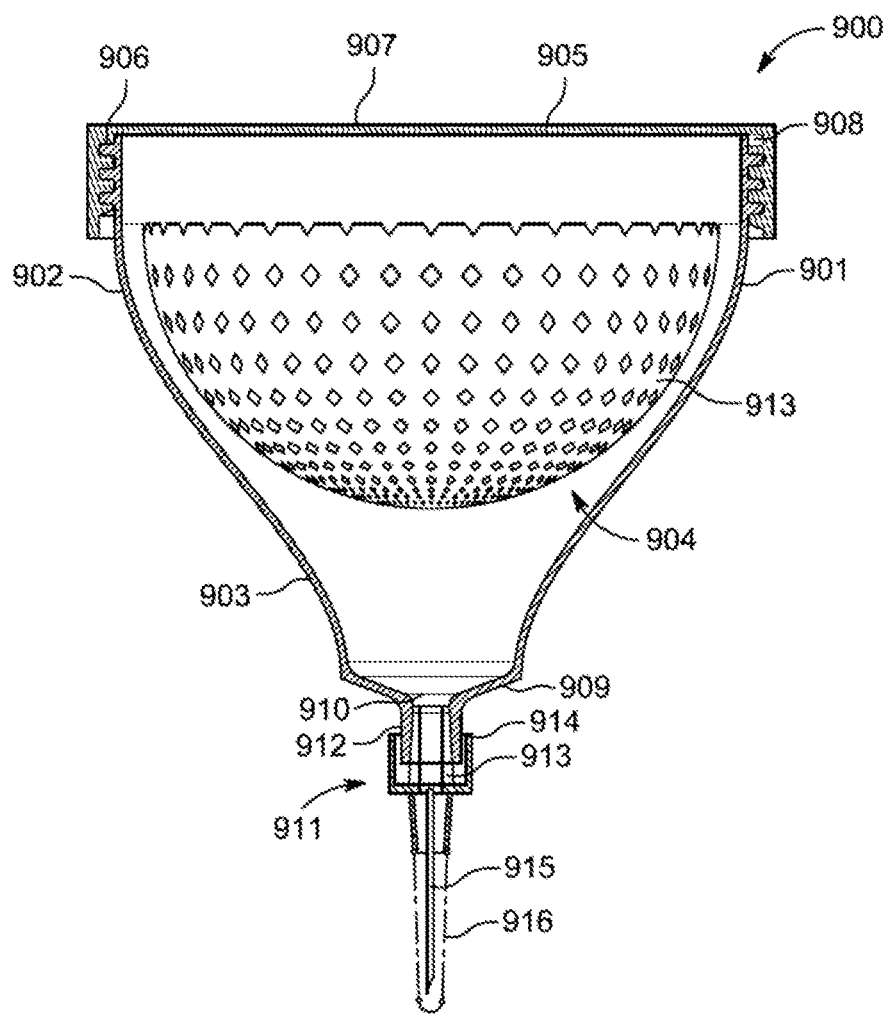
FIG. 9 is a side cross-sectional view of a portion of the exemplary oral fluid collection device using a luer lock mechanism to connect a hollow needle to a collection cup.

FIG. 9 is a side elevation view of an exemplary subassembly for use in an oral fluid collection device. This embodiment uses a luer lock mechanism to connect a hollow needle to a collection cup. The subassembly 900 has a collection cup 901 with a top end 902 and a bottom end 903. The collection cup 901 has an interior 904 and the top end 902 forms an opening 905 into the interior 904. The top end 902 of the collection cup 901 has threads 906 around the opening 905 engaging a screw-on cap 907 having threads 908. The underside 909 of the bottom end 903 has an opening 910 and a luer lock mechanism 911 to attach a hollow needle to the opening 910. A hollow female receptacle 912 of the luer lock mechanism 911 is attached to the opening 910. A hollow male insert 913 of the luer lock mechanism 911 is insertable into the hollow female receptacle 912 and can be locked thereto with a locking mechanism 914, as is well known in the art. A hollow needle 915 is attached to the hollow male insert 913 so that fluid in the collection cup 901 will flow from the collection cup 901, through the opening 910, through the hollow female receptacle 912, through the hollow male insert 913, through the hollow needle 915, and into a vacuum tube. The subassembly 900 functions similar to the description of the oral fluid collection devices 100 and 500 for obtaining a specimen in a clear vacuum tube. In the devices 100, 500 and subassembly 900, the vacuum tubes can be pushed manually onto the hollow needle and can be made of any suitable plastic or metal or combination thereof.

The oral fluid collection devices 100, 500 and subassembly 900 provide for useful methods for collecting oral fluids, saliva, or sputum. A collection cup is provided having a top end and a bottom end. The bottom end of the cup has one or more hollow needles extending from the bottom end of the cup. One or more vacuum tubes are provided. Each vacuum tube has a top end with a penetrable seal. The vacuum tubes are placed beneath the hollow needles. Oral fluids, saliva, or sputum from a donor are collected into the collection cup. The hollow needles are pushed through the penetrable seal of the vacuum tubes. The oral fluids, saliva, or sputum from the collection cup are drawn through the hollow needles and into the vacuum tubes. Preferably, the fluids, saliva, or sputum are collected up to a control line on the collection cup. If desired, a filter is placed in the collection cup and the oral fluids, saliva, or sputum are filtered before pushing the hollow needles through the penetrable seal of the vacuum tubes. A compressible sleeve can be placed over the hollow needles to prevent unwanted drainage prior to pushing the hollow needles through the penetrable seal of the vacuum tubes.

These oral fluid collection devices 100, 500 and subassembly 900 are used to collect oral fluids, such as mixed saliva, directly from a mouth of a donor. Mixed saliva is considered a gold standard for testing saliva because it provides the purest specimen by the donor. The use of mixed saliva is in compliance with the DHHS Regulations. The oral fluid collection device 500 with a pair of vacuum tubes 525 can also provide split specimen collection.

The specimen can be initially filtered through a non-absorbent material screen at the top of the oral fluid collection cup to remove bubbles, foam, particulates, and donor induced adulterants. The collection cup can have a scratch and a sniff food grade scent sticker on its side, or supplied to the collector, to excite the donor's salivary glands so that a sufficient volume of oral fluid may be obtained to reach a control line within 5 to 10 minutes. The vacuum tubes come pre-vacuumed to draw in a precise amount of oral fluid from the cup. The precise amount is defined by laboratory requirements and/or accrediting agencies including but not limited to the DHHS Regulations and other similar regulations, such as, for example, regulations of the Federal Department of Transportation ("DOT") and similar federal and state agencies. The vacuum tubes may be prefilled with a transport and stabilizing buffer to preserve the integrity of the specimen for a number of days stated by the buffer manufacturer in an un-refrigerated state. The vacuum tubes also preserve the integrity of the specimen for transport for laboratory testing, in compliance with proposed DHHS and/or DOT split specimen collection regulations. The filtered oral fluid specimen or split specimen contained in the leak proof vacuum tubes is optimized for immediate laboratory processing or frozen storage. The vacuum tube may also be used for point of collection (POCT) screening by placement of color-coded activated reagents in the vacuum test tube. The reagents react quickly to multiple possible substances in the donor's oral fluid as the oral fluid is vacuumed from the collection cup into analytical laboratory equipment.

Advances in nanotechnology, diagnostic and molecular imaging of nanoparticles, such as by use of gold nanoparticles, quantum dots, magnetic nanoparticles, etc. combined with mobile fluorescence devices, are especially well suited to use transparent vacuum tube delivered neat oral fluid specimens. The oral fluid specimen in the transparent vacuum tube allows for the use of lasers, fluorescence, and all nanotechnology diagnostic and molecular imaging of nanoparticle options which currently exist or which might exist in the future for a true solution ("Fluorometric virus detection platform using quantum dots-gold nanocomposites optimizing the linker links variation," published in ScienceDirect Volume 1109, 1 May 2020, pages 148-157, found at https://doi.org/10.1016/j.aca.2020.02.039). Oral fluid has long been understood to be useful as a diagnostic tool in medicine. Technological advances over the past decades have enabled oral fluid to expand its usefulness in the diagnosis of disease, prediction of disease progression, monitoring of therapeutic drug levels and detection of illicit drugs. The easy non-invasive nature of collection and the relationship between oral fluid and plasma levels make oral fluid a valuable clinical tool. ("Oral fluid as a diagnostic tool," published in Clin Chem Lab Med 2004; 42(11):1273-1287, found at. DOI 10.1515/CCLM.2004.248).

For purposes of COVID-19 or other virus testing, the oral fluid collection devices 100, 500 and subassembly 900, for example, allow for the safe and secure self-collection and secure transport of either saliva, oral fluids and/or sputum collected from a donor. Recently, sputum has been shown in scientific studies to have a higher recovery rate of the COVID-19 markers compared to a nasal swab, which has a higher than expected false negative rate and which is extremely invasive. ("Detection of SARS-CoV-2 in Different Types of Clinical Specimens," JAMA Research Letter published Mar. 11, 2020 found at:25 doi:10.1001/jama.2020.3.3786 and "SARS-CoV-2 more readily detected in induced sputum than in throat swabs of convalescent COVID-19 patients," Mar. 12, 2020 in The Lancet Infectious Diseases found at DOI: http://doi.org/10.1016/S1473-3099(20)30174-2). Likewise, there is a recent medical study showing that a saliva specimen is a consistent detection option for COVID-19 patients. The 2019 novel coronavirus (2019-nCoV) was detected in the self-collected saliva of 91.7% (11/12) of patients. Serial saliva viral load monitoring generally showed a declining trend. Live virus was detected in saliva by viral culture. Saliva is a promising noninvasive specimen for diagnostic, monitoring, and 35 infectious control in patients with 2019-nCoV. ("Consistent Detection of 2019 Novel Coronavirus in Saliva," published 30 Feb. 12, 2020 in the Journal for Infectious Diseases Society of America found at DOI: 10.1093/cid/ciaa149).

Because the oral fluid collection devices 100, 500 and subassembly 900 are self-collection devices, collection of specimens can be conducted without placing a healthcare worker at risk of contracting COVID-19. The devices allow for multiple oral fluid collection possibilities based upon compliance with various pre-collection protocols and instructions from the collector. Multiple oral fluid collections make the devices ideal for collection of oral fluid specimens to measure the donor's antibody production following a bout with COVID-19. The devices are also useful following vaccination (once discovered) to determine the donor's level of immunity protection against a subsequent outbreak and to provide clearance to go safely back to work and play in a non-social distancing society.

Figure 10:
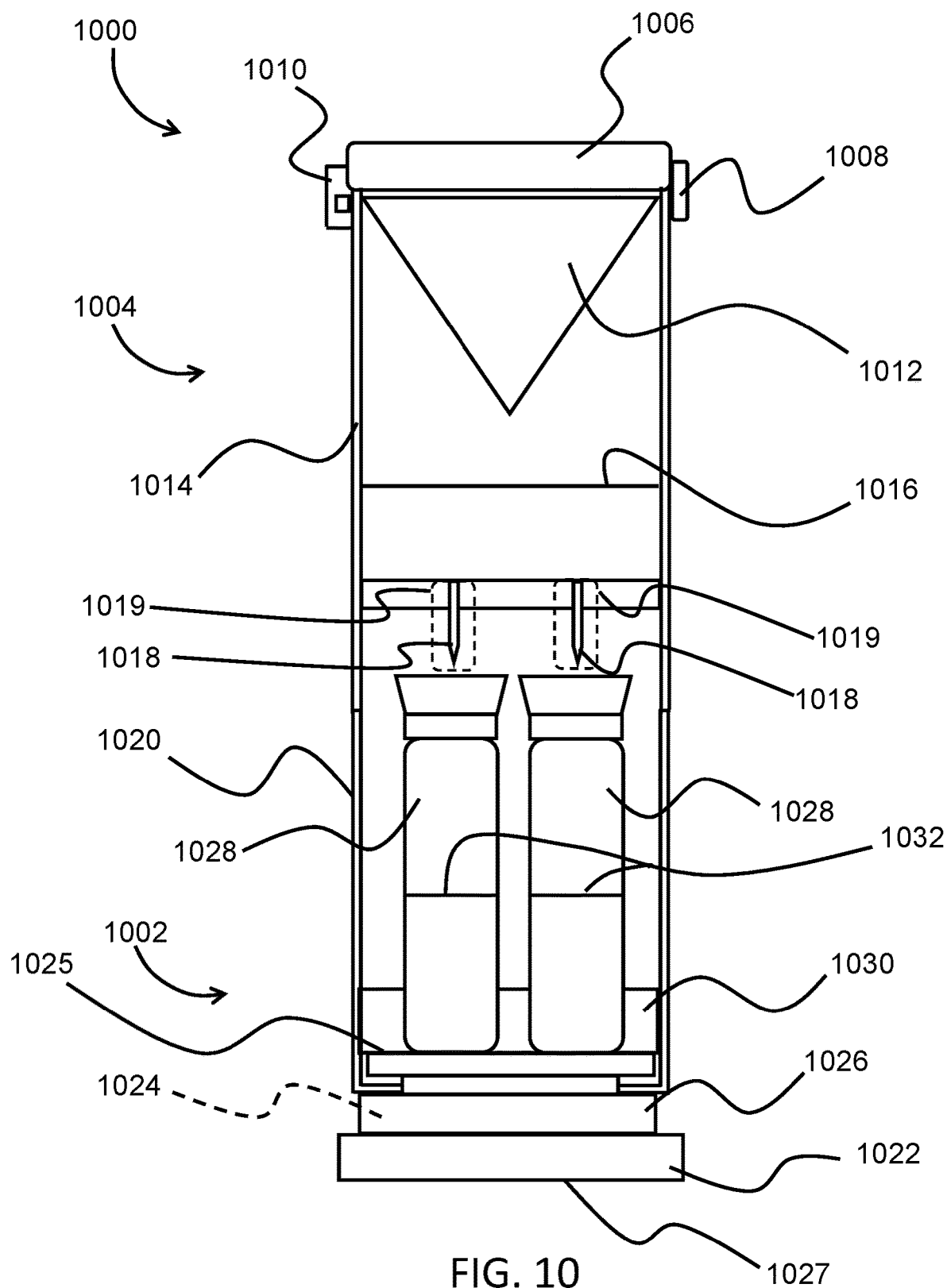
FIG. 10 is a schematic illustration of another exemplary embodiment of an oral fluid collection device of the present disclosure.

FIGS. 10-21 schematically illustrate another embodiment of an oral fluid collection device 1000. The fluid collection device 1000 operates generally on the same principles as described herein for other oral fluid collection devices 100 and 500 and includes a pair of vacuum tubes that collect split samples. However, the oral fluid collection device 1000 illustrated in FIGS. 10-21 includes a sliding or plunger mechanism for facilitating relative linear movement between the vacuum tubes and hollow needles to collect samples in the vacuum tubes. As illustrated in FIG. 10, the oral fluid collection device 1000 includes a base 1002, a collection cup 1004, and a cap 1006. The cap 1006 is connected to the collection cup 1004 by a hinge 1008 and a user can selectively open or close the cap 1006 to gain access to or secure the collection cup 1004. Such cap 1006 is secured to the collection cup 1004 by a reversible protrusion and snap mechanism 1010. Positioned in the collection cup 1004 is an anti-foaming filter funnel 1012 for filtering oral fluids deposited in the collection cup 1004 by a donor. A collection cup 1004 includes a thin walled body 1014 that defines the inner volume or the collection cup 1004. A collection cup fill line 1016 can be scribed on the collection cup body 1014 to assist a user in determining when a sufficient amount of oral fluid has been deposited in the collection cup 1004. The collection cup 1004 further includes a pair of hollow needles 1018 that are secured in a vertical position at least partially within the collection cup 1004 and in fluid communication with oral fluid deposited into the collection cup 1004. As previously described, a flexible, compressible, penetrable sleeve 1019 can be positioned over each hollow needle 1018 to prevent unwanted drainage through the hollow needle 1018 and to offer protection to a user or donor handling the oral fluid collection device 1000 from injury from the sharp end of the hollow needle 1018.

The base 1002 includes a thin walled body 1020 that defines the inner volume of the base 1006. The thin walled body 1014 of the collection cup 1004 and the thin walled body 1020 of the base 1002 are reversibly secured together by a removeable seal. During the collection of oral fluids, the thin walled body 1014 of the collection cup 1004 and the thin walled body 1020 of the base 1002 remain secured together. After the collection of oral fluids is complete and the oral fluids are fully moved to and stored in vacuum tubes, the removeable seal can be removed, the collection cup 1004 and the base 1002 separated, and the vacuum tubes accessed and removed by the donor or other user of the oral fluid collection device 1000.

Figure 17:
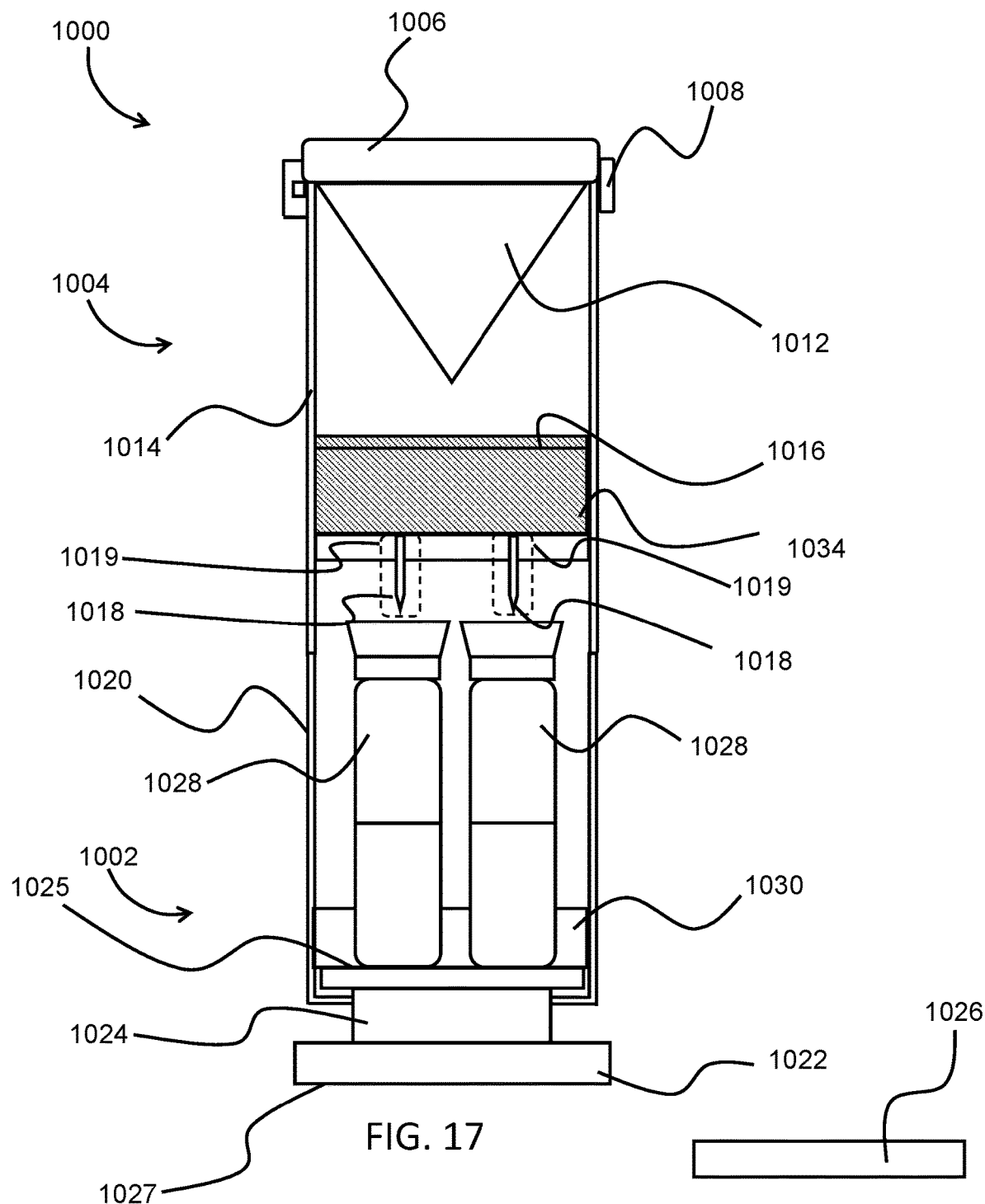
FIG. 17 is a schematic illustration of the oral fluid collection device of FIG. 10 in use by a donor.

The base 1002 includes a pedestal 1022, which forms the bottom portion of the base 1002. The pedestal 1022 includes an upper surface 1025 and a lower surface 1027 and a recessed section 1024 located between the upper surface 1025 and lower surface 1027 (as best illustrated in FIG. 17). As illustrated in FIG. 10, a removable tab 1026 is positioned within the recessed section 1024 and, as will be subsequently described, the removeable tab 1026 engages with the recessed section 1024 in a manner that maintains a static positional relationship between the vacuum tubes 1028 and the hollow needles 1018. Such a static positional relationship prevents the vacuum tubes 1028 from interaction with the hollow needles 1018 prematurely (i.e., prevents accidental piercing of the membrane sealing the vacuum tubes prior to the oral fluid being in proper position to fill the vacuum tubes). As illustrated in the figures, positioned within the base 1002 are a pair of vacuum tubes 1028, which can be optionally reversibly secured in place with a vacuum tube holder 1030. Each vacuum tube 1028 can also include a vacuum tube fill line 1032 to inform a user whether a sufficient amount of oral fluid has been deposited into the vacuum tubes 1028.

Figure 11:
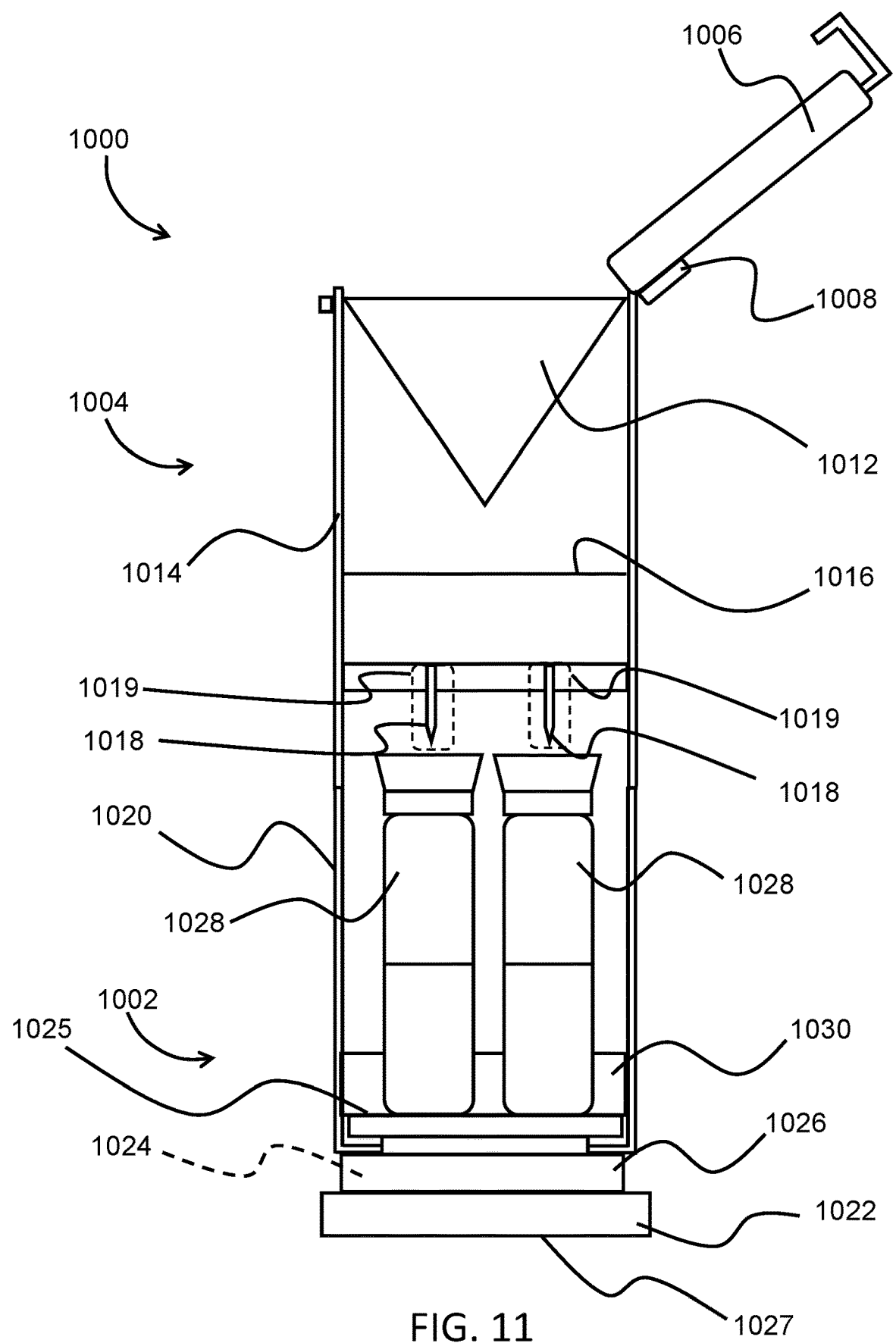
FIG. 11 is a schematic illustration of the oral fluid collection device of FIG. 10 in preparation for use by a donor.
Figure 12:
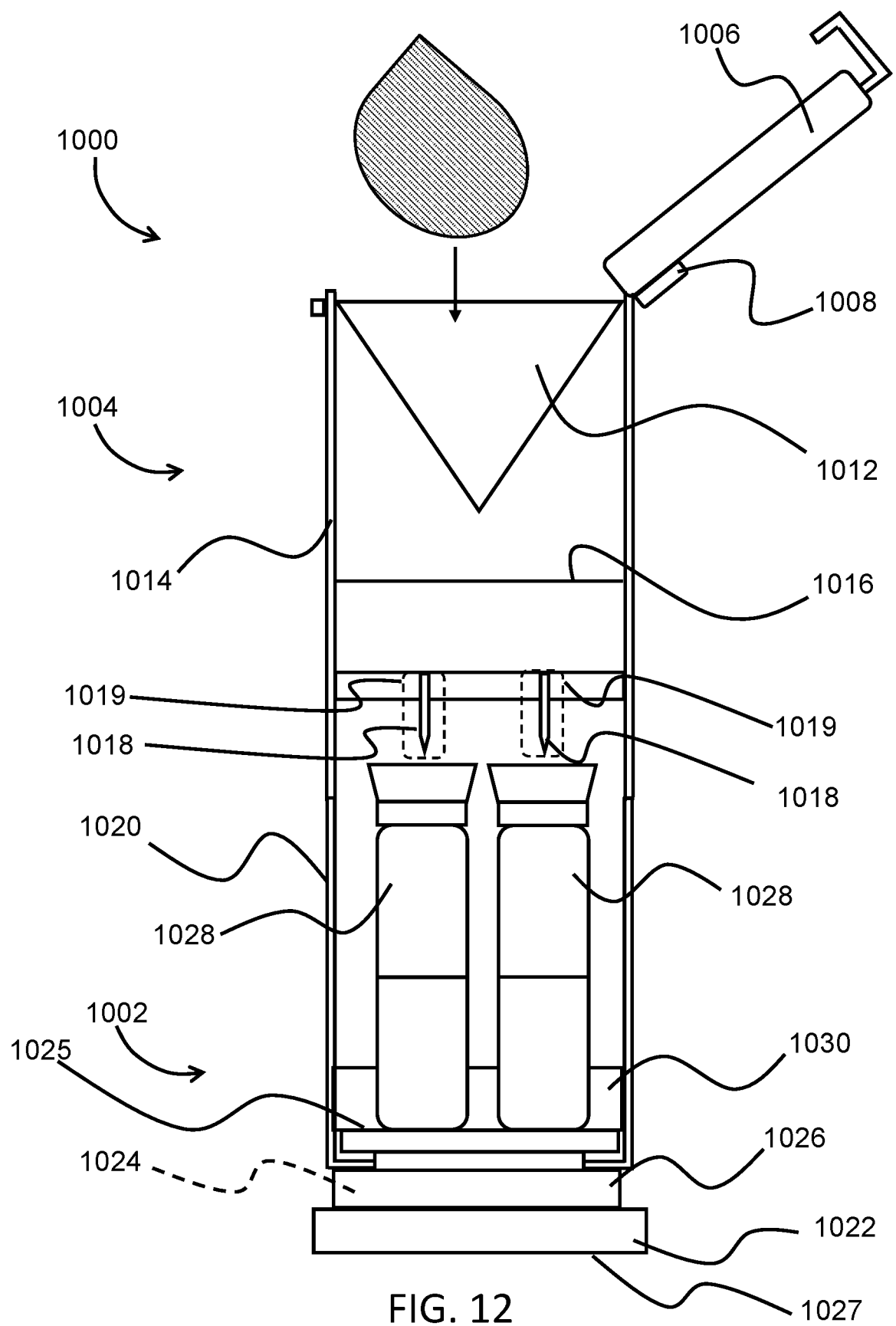
FIG. 12 is a schematic illustration of the oral fluid collection device of FIG. 10 in use by a donor.
Figure 13:
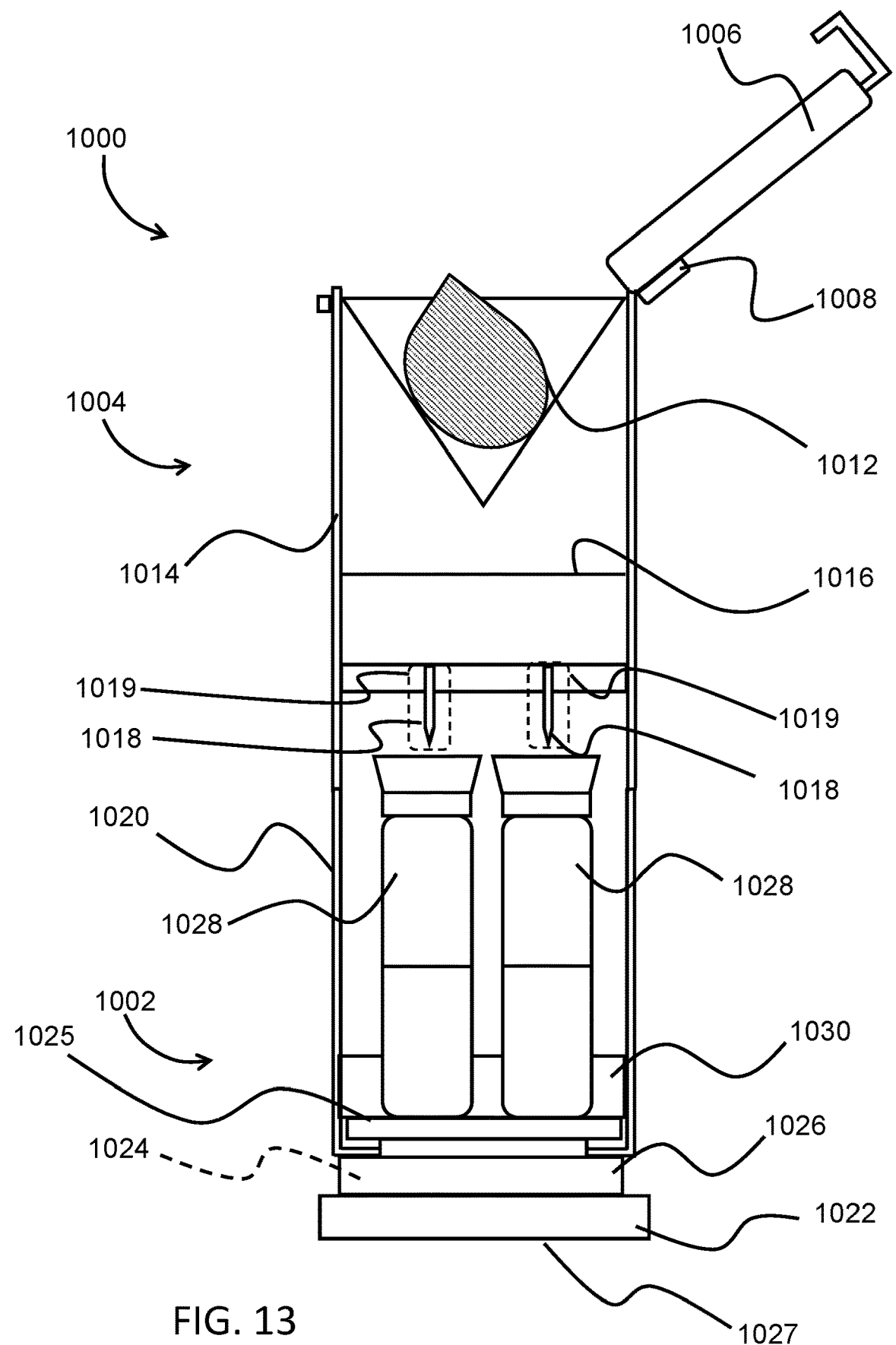
FIG. 13 is a schematic illustration of the oral fluid collection device of FIG. 10 in use by a donor.
Figure 14:
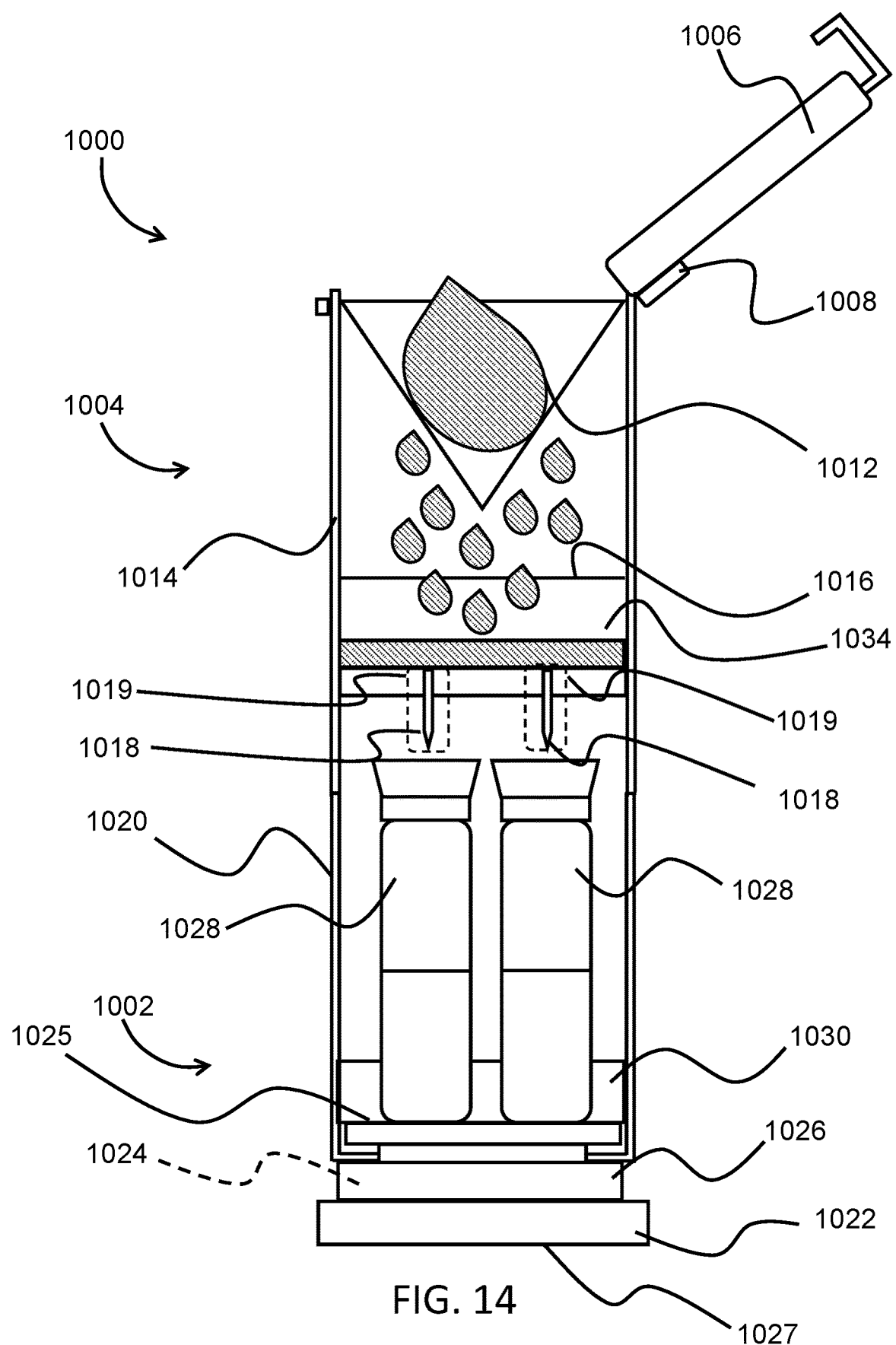
FIG. 14 is a schematic illustration of the oral fluid collection device of FIG. 10 in use by a donor.
Figure 15:
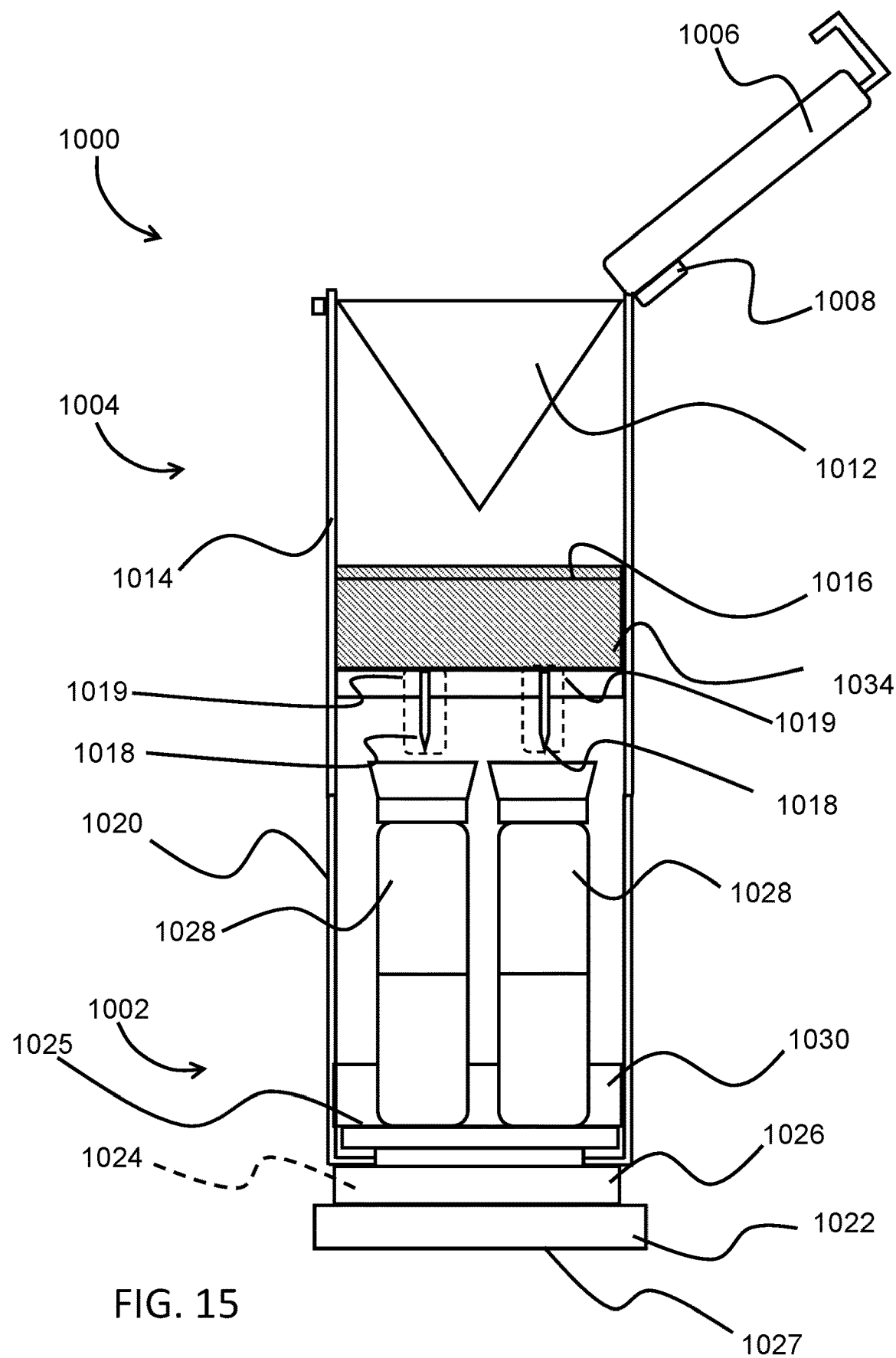
FIG. 15 is a schematic illustration of the oral fluid collection device of FIG. 10 in use by a donor.

FIGS. 11-21 illustrate an exemplary method of using the oral fluid collection device 1000. As illustrated in FIG. 11, when a donor is ready to use the oral fluid collection device 1000, the donor will unsecure the protrusion and snap mechanism 1010 and rotate the cap 1006 about the hinge 1008 to open the oral fluid collection device 1000. As illustrated in FIG. 12, the donor deposits oral fluid into the opening in the oral fluid collection device 1000. As the oral fluid is deposited into the oral fluid collection device 1000, it engages the filter funnel 1012 (as illustrated in FIG. 13), where the filter funnel 1012 filters out unwanted materials from the oral fluid. The oral fluid then progresses through filter funnel 1012 downward into a collection area 1034 (as illustrated in FIG. 14). As all the oral fluid filters through the filter funnel 1012 and into the collection area 1034, the collected fluid may surpass the fill line 1016 on the collection cup 1004 (as illustrated in FIG. 15). If the oral fluid in the collection area 1034 does not surpass the fill line 1016 of the collection cup 1004 with the first oral fluid deposit from the donor, the donor can again deposit oral fluid into the oral fluid collection device 1000 until the oral fluid surpasses the fill line 1016.

Figure 16:
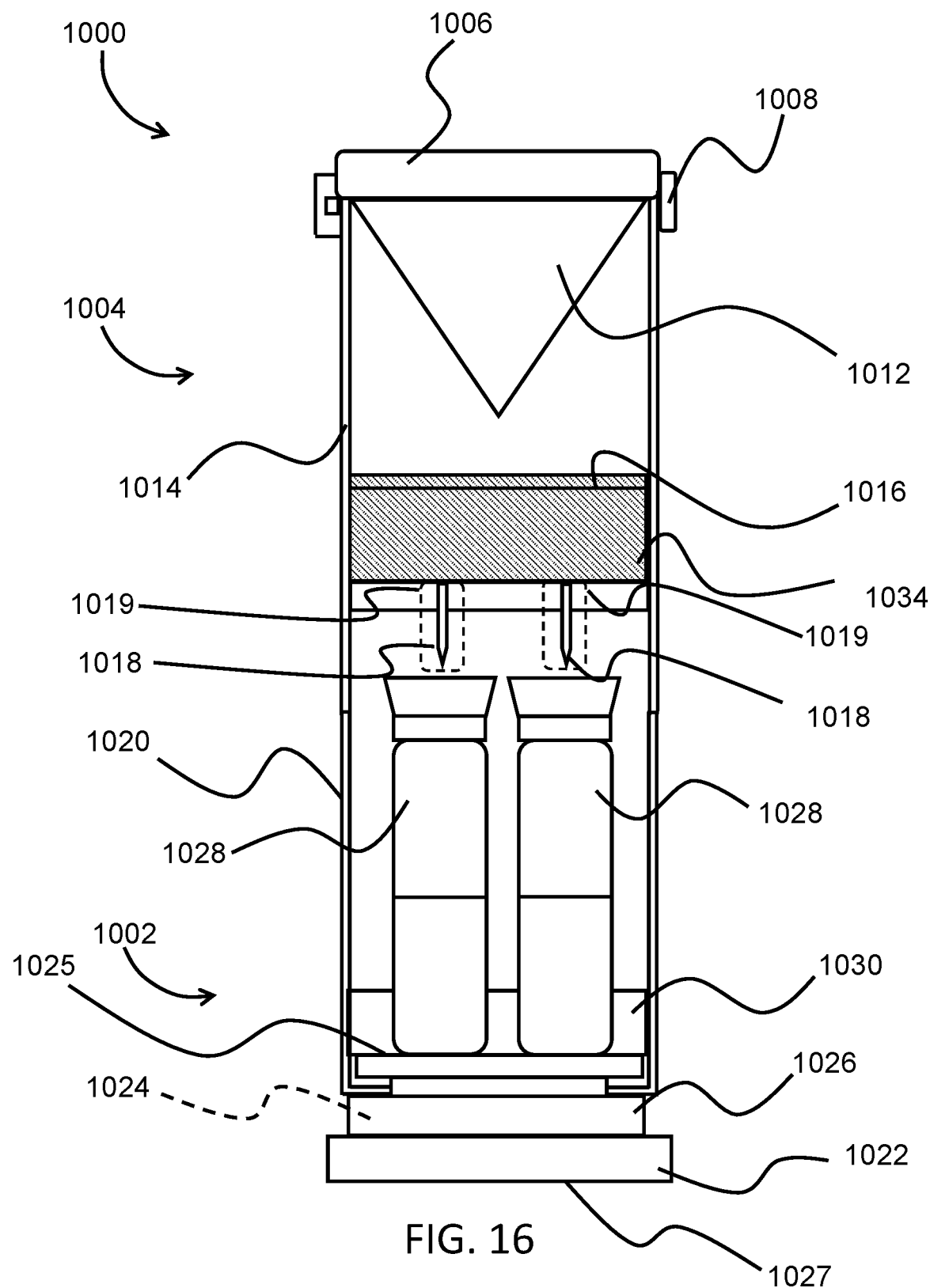
FIG. 16 is a schematic illustration of the oral fluid collection device of FIG. 10 in use by a donor.
Figure 18:
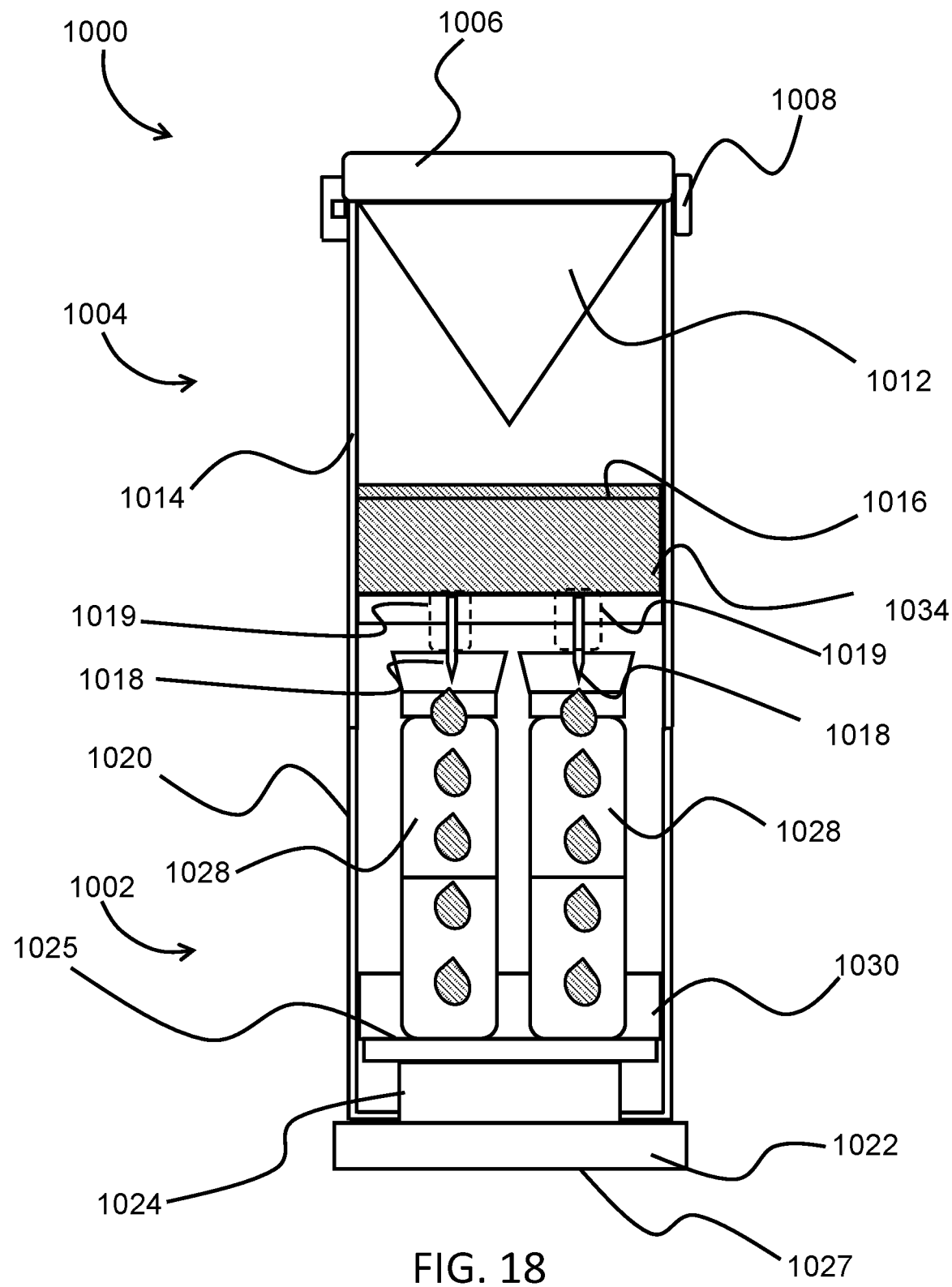
FIG. 18 is a schematic illustration of the oral fluid collection device of FIG. 10 in use by a donor.
Figure 19:
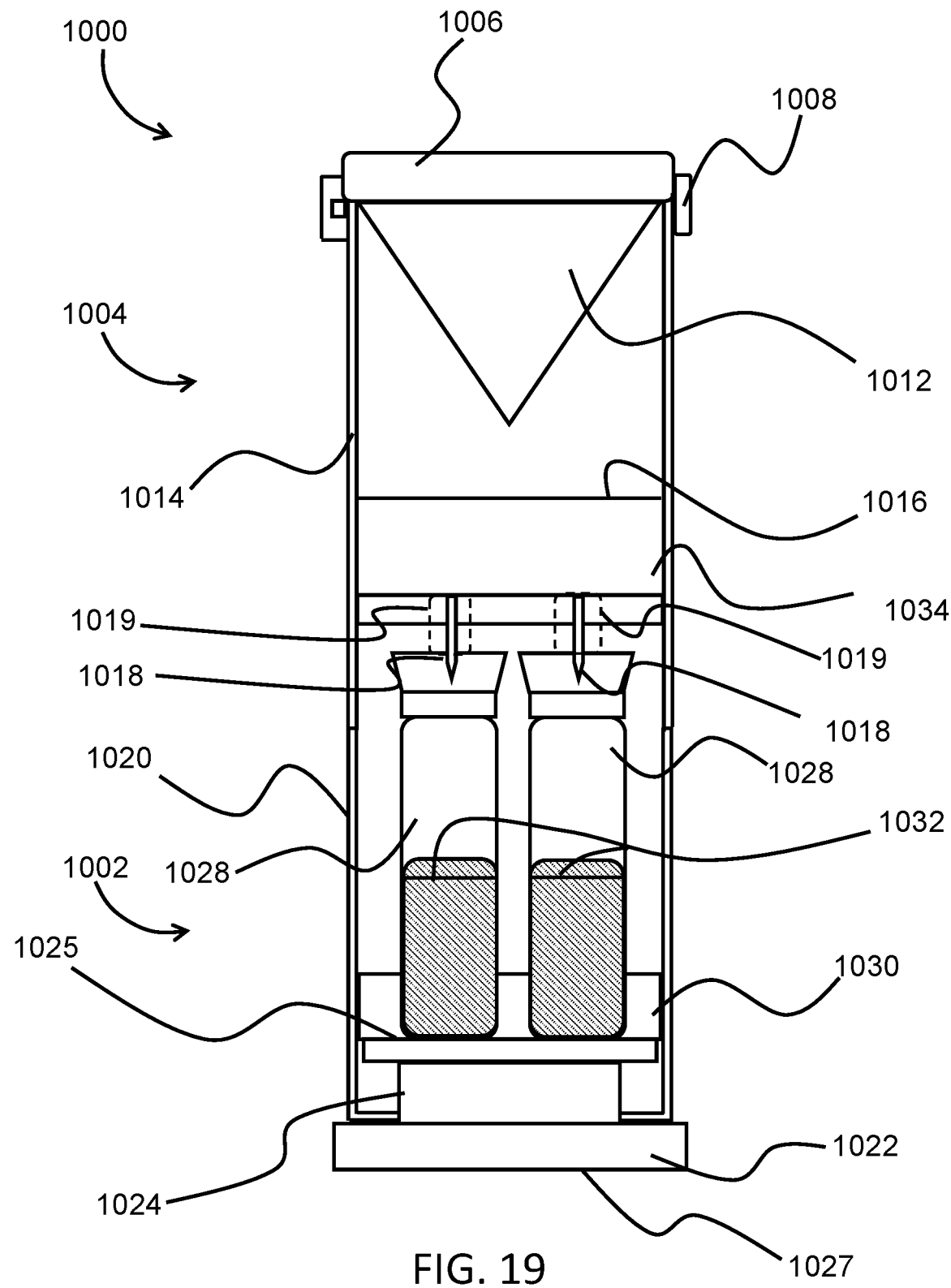
FIG. 19 is a schematic illustration of the oral fluid collection device of FIG. 10 in use by a donor.

Once the fill line 1016 on the collection cup 1004 is surpassed, the cap 1006 is closed and latched (as illustrated in FIG. 16) and the removable tab 1026 is removed from the recessed section 1024 of the pedestal 1022 (as illustrated in FIG. 17). The oral fluid collection device 1000 is now in condition to fill the vacuum tubes 1028 with oral fluid in the collection area 1034. As illustrated in FIG. 18, with the removable tab 1026 removed, the collection cup 1004 and thin walled body 1020 of the base 1002 can move downward relative to the vacuum tubes 1028. Such movement moves the hollow needles 1018 downward and engages the hollow needles 1018 with the vacuum tubes 1028; thus, facilitating the flow of oral fluid from the collection area 1034 into the vacuum tubes 1028. As all the oral fluid flows from the collection area 1034 into the vacuum tubes 1028, the oral fluid will surpass the vacuum tube fill lines 1032 (as illustrated in FIG. 19).

Figure 20:
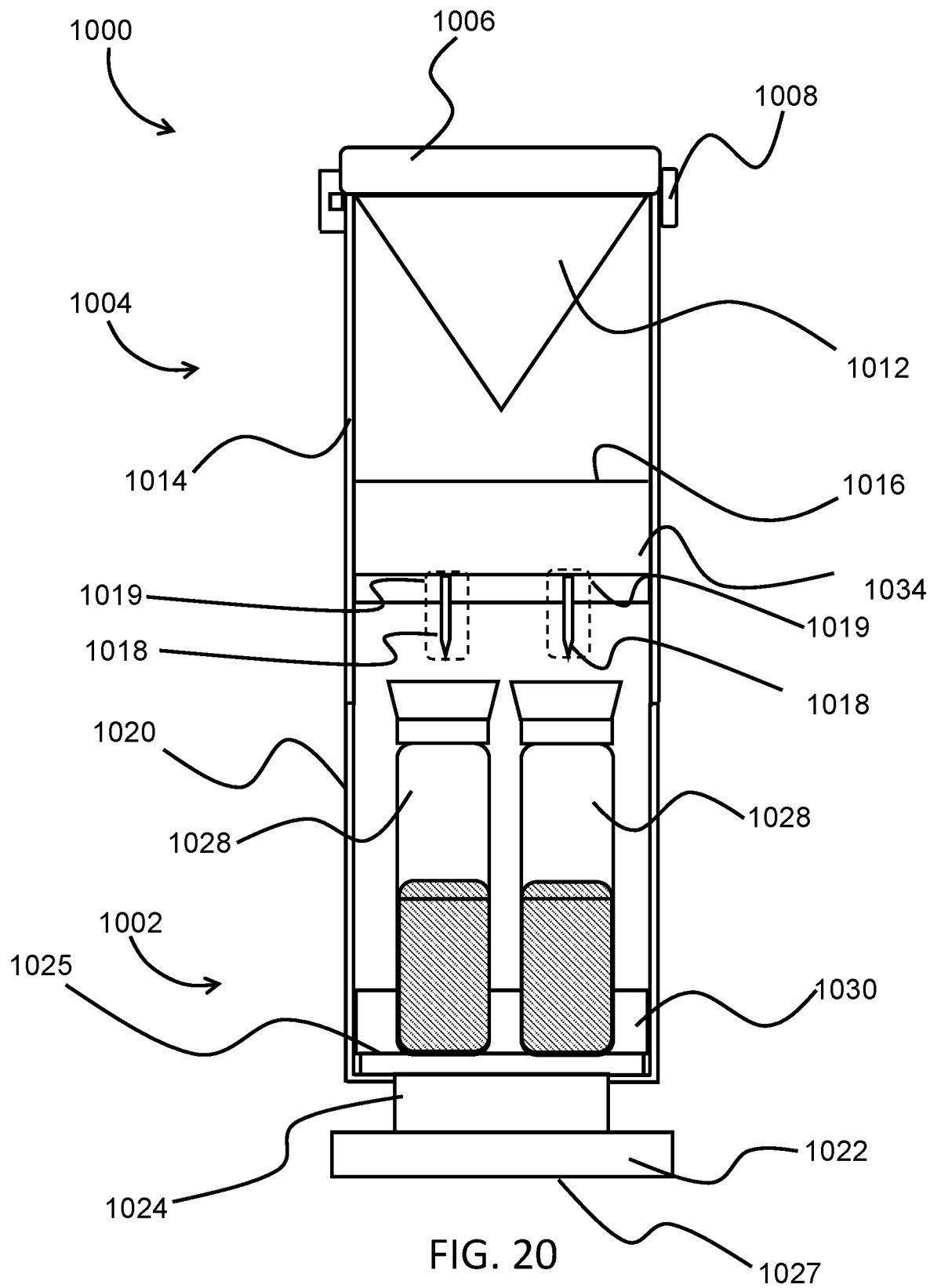
FIG. 20 is a schematic illustration of the oral fluid collection device of FIG. 10 in use by a donor.
Figure 21:
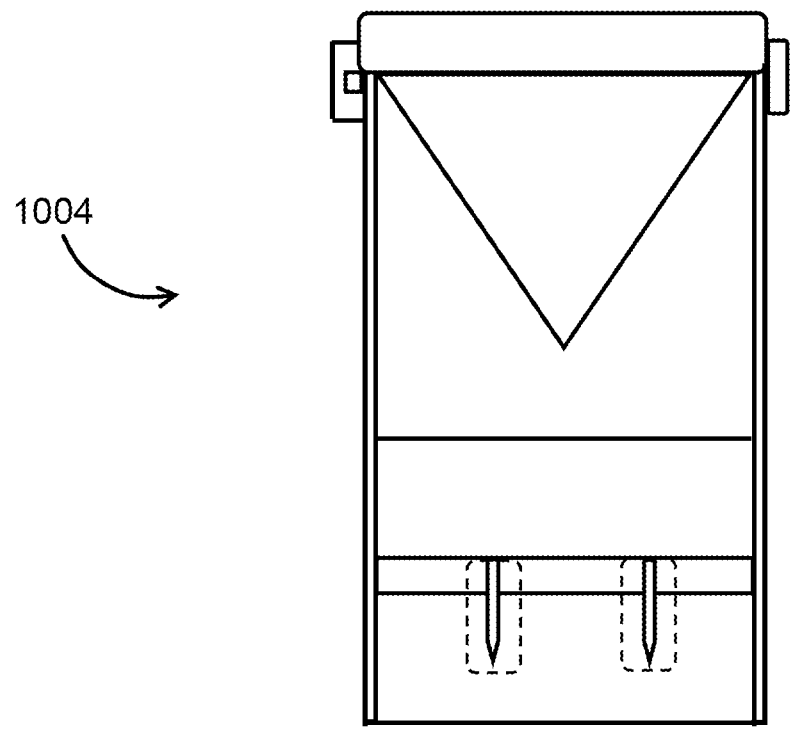
FIG. 21 is a schematic illustration of the oral fluid collection device of FIG. 10 in use by a donor.
Figure 21:
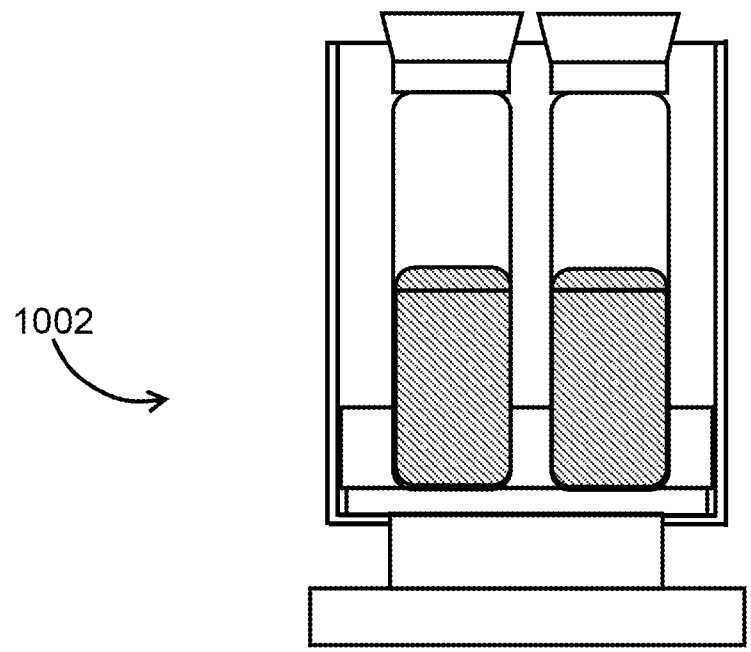

One method of moving the collection cup 1004 and thin walled body 1020 of the base 1002 downward relative to the vacuum tubes 1028 is to place the oral fluid collection device 1000 on a flat surface, such as a table top, with the lower surface 1027 of the pedestal 1022 in contact with the flat surface, and apply downward pressure on the top of the oral fluid collection device 1000 until the hollow needles 1018 engage with the vacuum tubes 1028 and oral fluid flows into the vacuum tubes 1028. Once the vacuum tubes 1028 are filled, the oral fluid collection device 1000 can be returned to its original position (as illustrated in FIG. 20), any seal or mechanism joining the collection cup 1004 to the base 1002 is removed and the collection cup 1004 can be separated from the base 1002 (as illustrated in FIG. 21). The vacuum tubes 1028 can now be removed from the base 1002 and secured and packaged for shipping or transport to a laboratory for testing. Once the vacuum tubes are removed and secured, both the base 1002 and the collection cup 1004 can be discarded.

In other embodiments of oral fluid collection devices, a base of such a device can include features that provide for accommodating vacuum tubes of different sizes. Additionally, components and features can be incorporated into an oral fluid collection device to facilitate the engagement and disengagement of vacuum tubes and hollow needles and to protect users from the hollow needles. Such components and features include the use of a force generated by the compression of a resilient material to manage the engagement of the hollow needle with the vacuum tube and the use of a force generated by the release of a compressed material to manage the disengagement of the hollow needle from the vacuum tube. FIGS. 22-31 illustrate exemplary components that add such features and functionality, which can be used with any of the embodiments disclosed herein.

Figure 22:
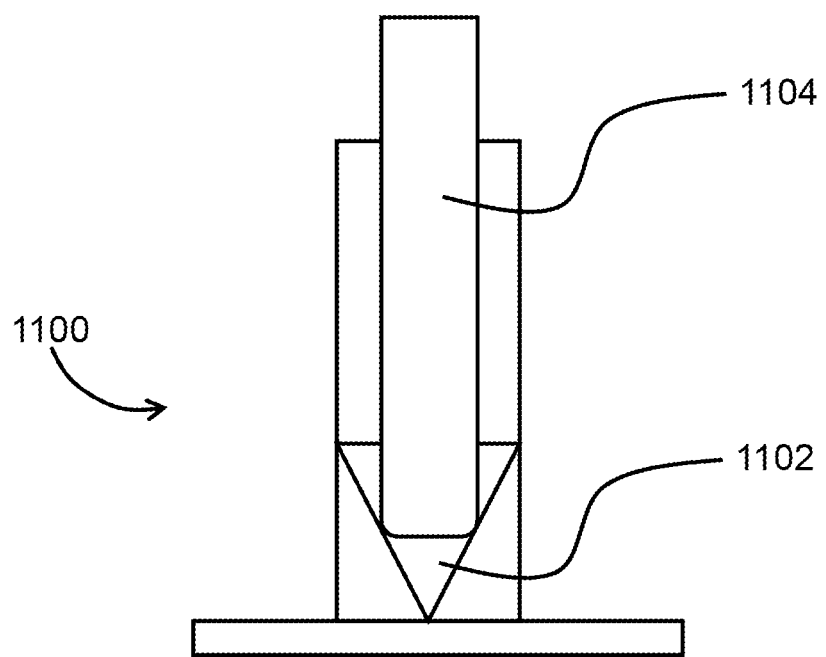
FIG. 22 is a schematic illustration of an exemplary base for use with an oral fluid collection device with a vacuum tube engaged with the base.
Figure 23:
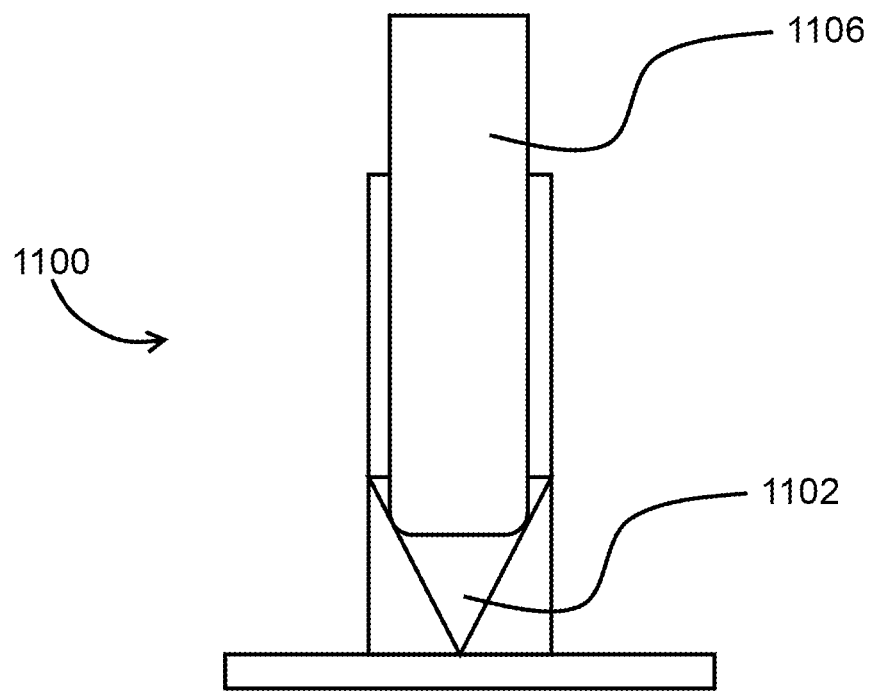
FIG. 23 is a schematic illustration of the exemplary base of FIG. 22, with another vacuum tube engaged with the base.

In one example of a base 1100, schematically illustrated in FIGS. 22 and 23, the base 1100 can include a feature to accommodate different sized vacuum tubes. The exemplary base 1100 includes a cone shaped feature 1102 that can form a friction fit with a vacuum tube inserted into the base 1100. As illustrated in FIG. 22, a vacuum tube 1104 with a relatively small diameter is accommodated by the cone-shaped feature 1102 in the base 1100. As illustrated in FIG. 23, a vacuum tube 1106 with a relatively large diameter is accommodated by the cone shaped feature 1102 in the base 1100. In addition to a cone shaped feature, the base can include a funnel shaped feature, a wedge shaped feature or any other shape that facilitates the insertion of a vacuum tube, including vacuum tubes of varying sizes.

Figure 24:
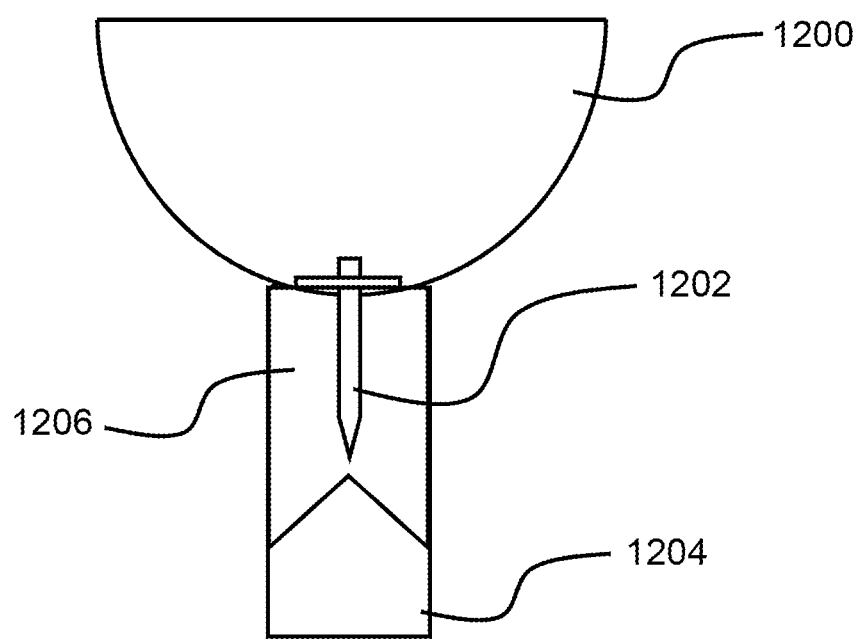
FIG. 24 is a schematic illustration of an exemplary collection cup and related accessories for use with an oral fluid collection device.
Figure 25:
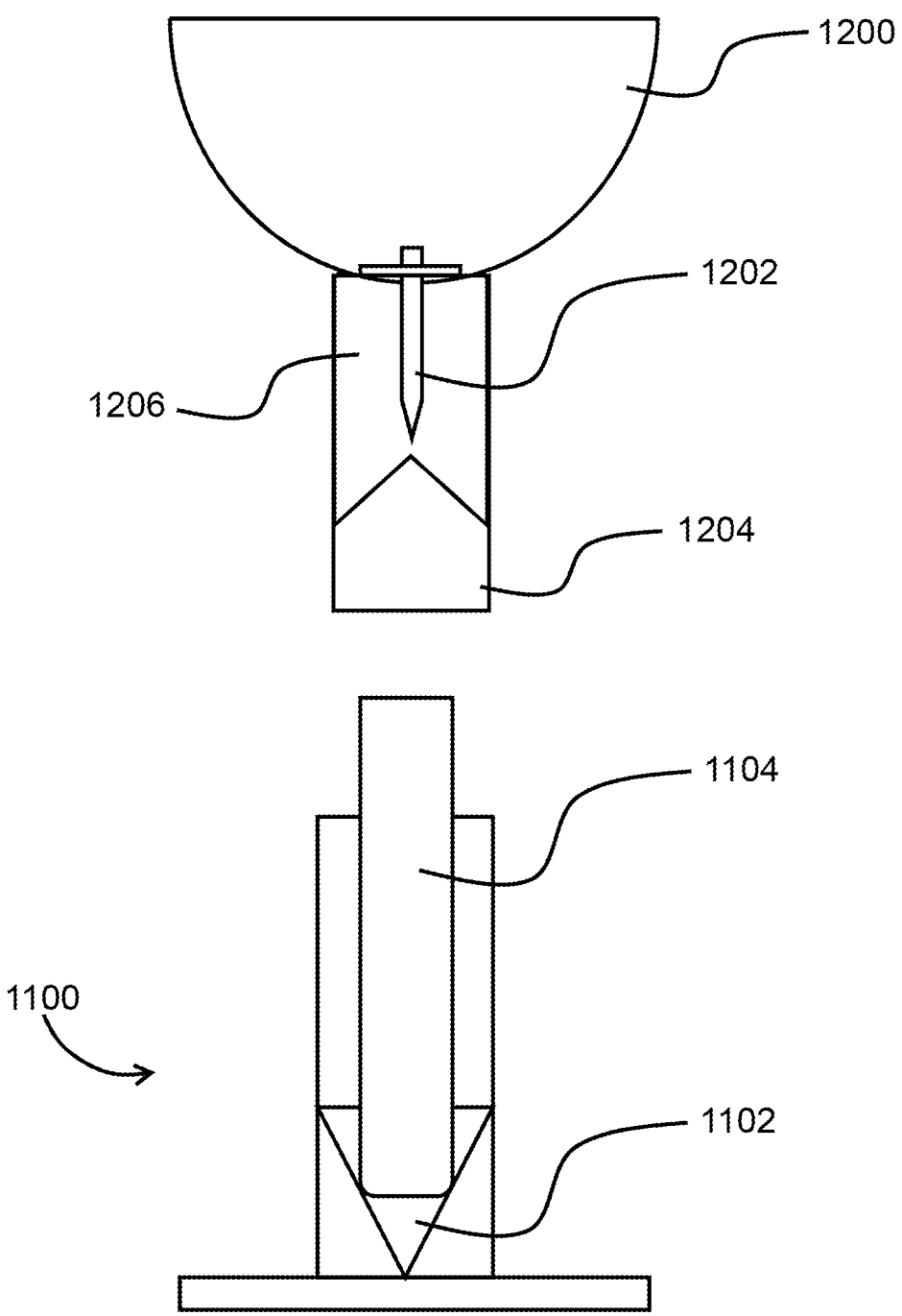
FIG. 25 is a schematic illustration of the exemplary collection cup of FIG. 24 in use with the exemplary base of FIG. 22.

FIG. 24 schematically illustrates an exemplary collection cup 1200 with an integrated hollow needle 1202 and a tube guide 1204 extending downward from the collection cup 1200 and enclosing the hollow needle 1202. Positioned within the tube guide 1204, and surrounding the hollow needle 1202, is a compressible and resilient sleeve 1206. The sleeve 1206 consists of a material that can be deformed by an applied force, but will return to its original shape upon the removal of the force. Once such material is polypropylene; however, it will be understood that many materials can be used for the sleeve 1206. As illustrated in FIG. 24, the sleeve 1206 occupies the available volume of the tube guide 1204 and extends beyond the hollow needle 1202; thus, protecting both the hollow needle 1202 and any user or donor that handles the oral fluid collection device. Similar to the flexible, compressible, penetrable sleeves 116, 1019 described above, the compressible and resilient sleeve 1206 illustrated in FIGS. 24-31 can prevent unwanted drainage through the hollow needle 1202.

Figure 26:
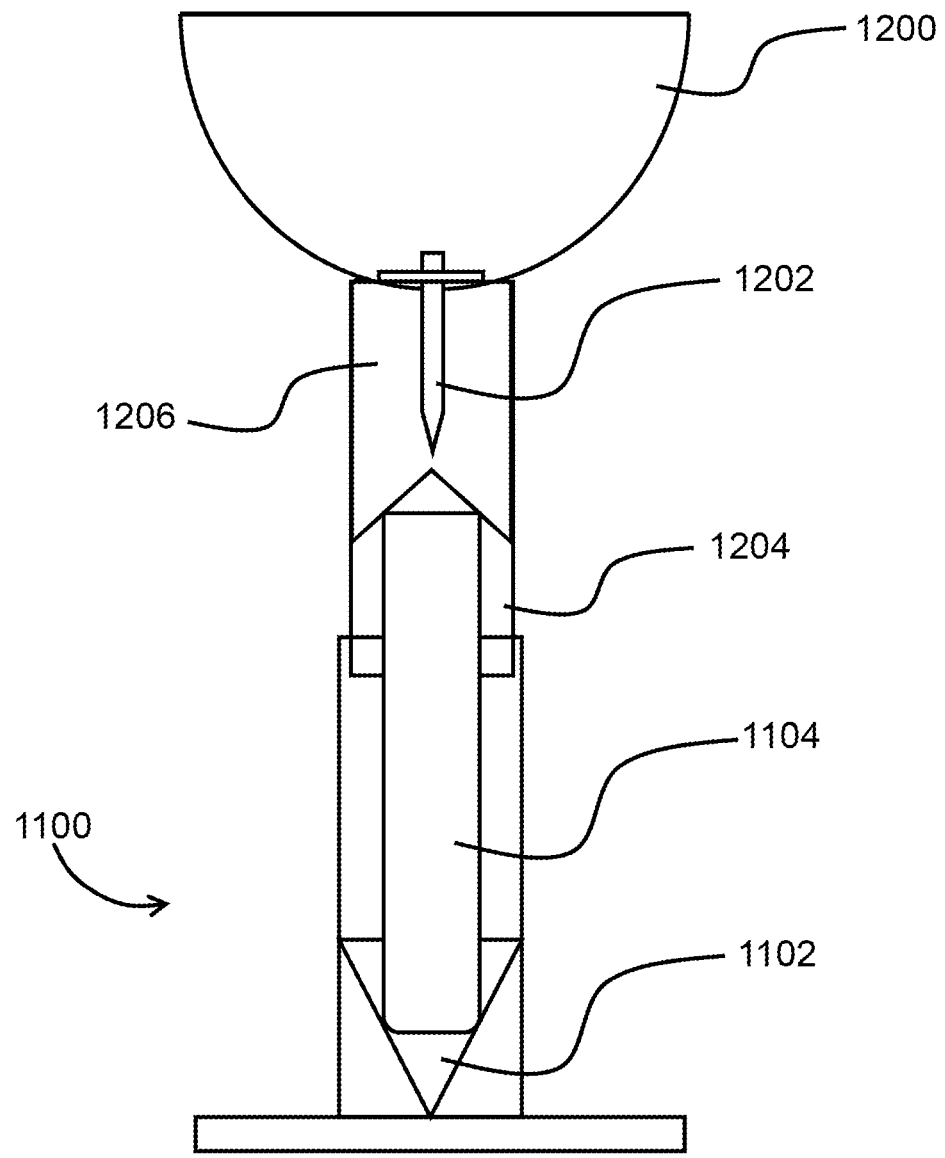
FIG. 26 is a schematic illustration of the exemplary collection cup of FIG. 24 in use with the exemplary base of FIG. 22.
Figure 27:
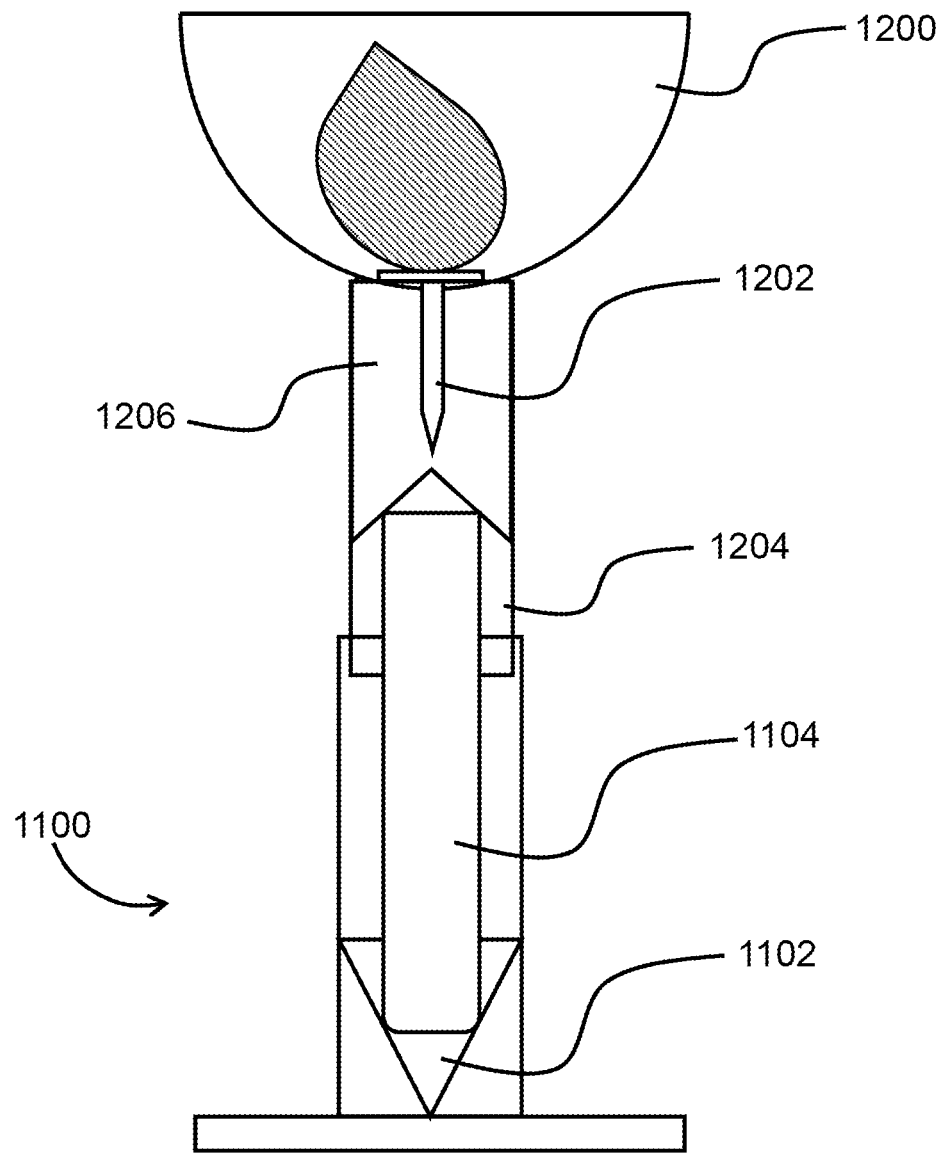
FIG. 27 is a schematic illustration of the exemplary collection cup of FIG. 24 in use with the exemplary base of FIG. 22.
Figure 28:
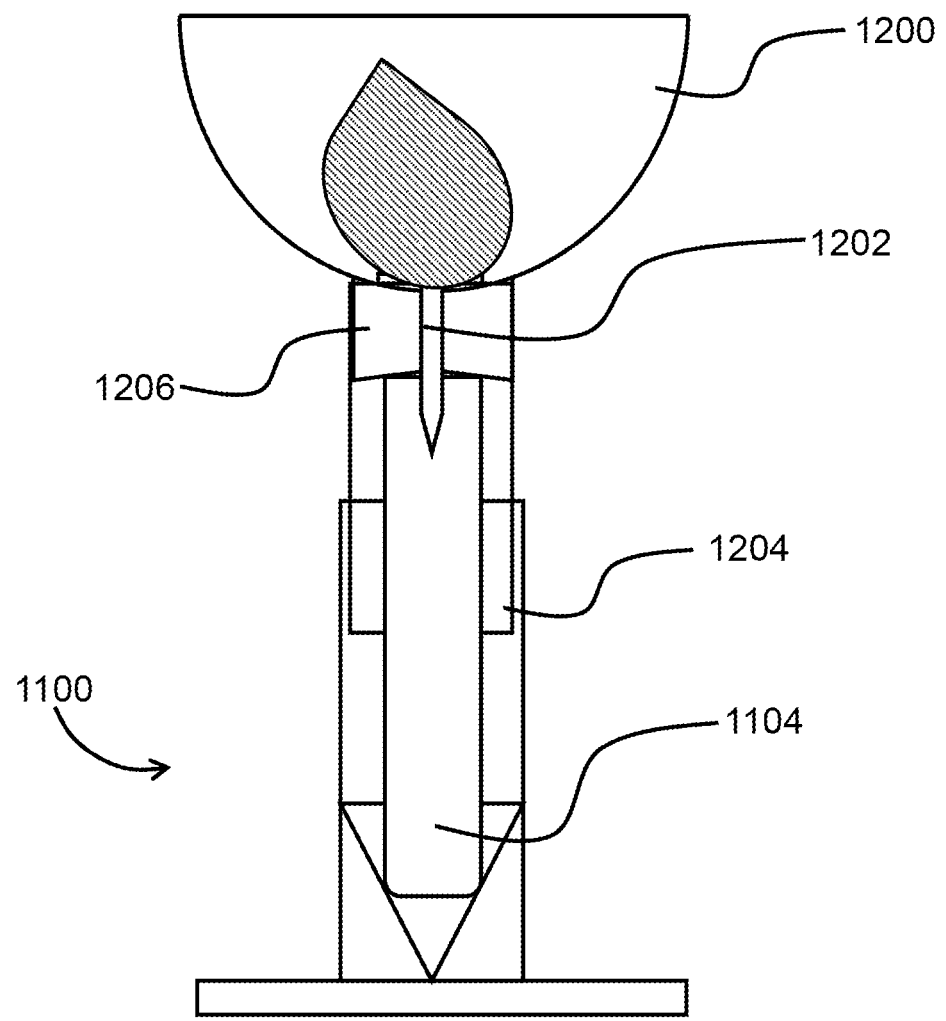
FIG. 28 is a schematic illustration of the exemplary collection cup of FIG. 24 in use with the exemplary base of FIG. 22.
Figure 29:
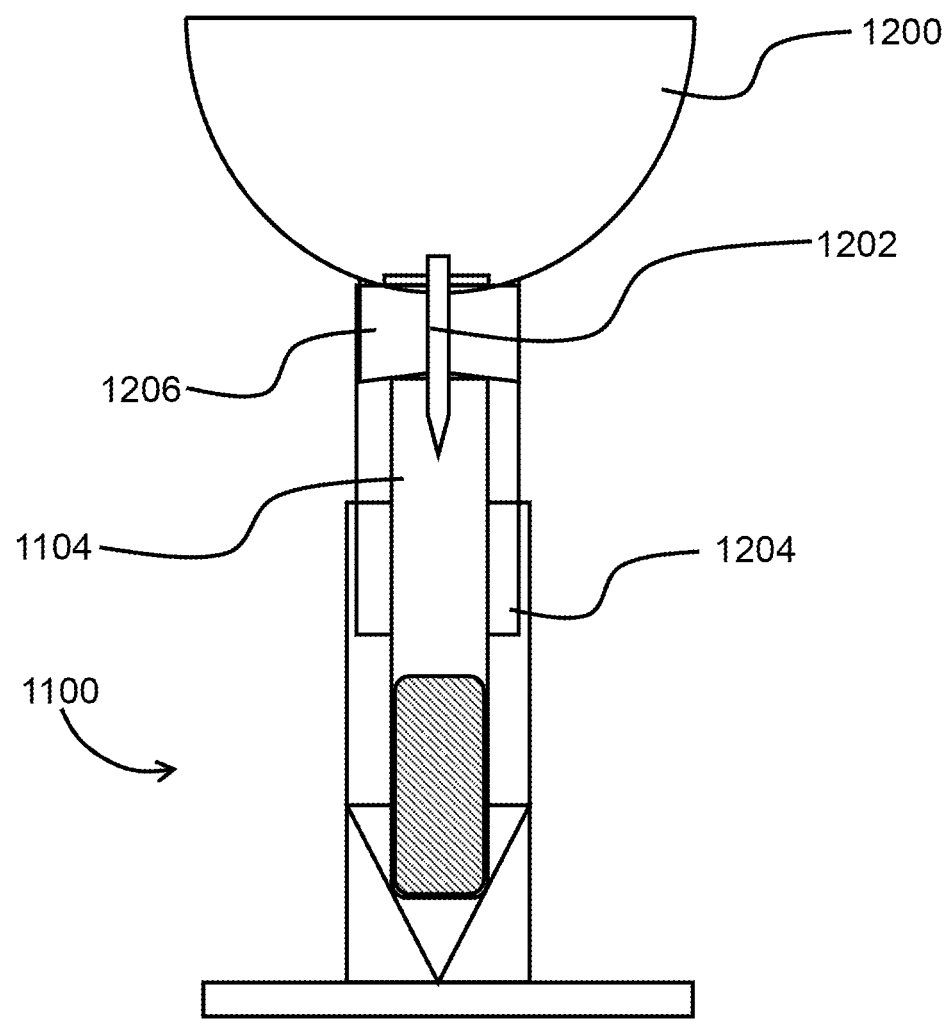
FIG. 29 is a schematic illustration of the exemplary collection cup of FIG. 24 in use with the exemplary base of FIG. 22.

FIGS. 25-31 schematically illustrate the combination of the base 1100 of FIGS. 22 and 23, and the collection cup 1200 and related components of FIG. 24. When the base 1100 and collection cup 1200 (and related components) are to be used together, a user positions the collection cup 1200 over the base 1100, with a vacuum tube 1104 positioned in the base 1100. As illustrated in FIG. 26, the collection cup 1200 is lowered toward the base 1100, and the tube guide 1204 is slid over the vacuum tube 1104 and into the base 1100. The collection cup 1200 is lowered until the top of the vacuum tube 1104 is positioned near the bottom of the sleeve 1206. Once in such a position, as illustrated in FIG. 27, the donor can deposit a specimen in the collection cup 1200. Once a sufficient volume of oral fluid is deposited in the collection cup 1200, the user or donor can further move the collection cup 1200 downward, applying enough force to overcome the resilient nature of the sleeve 1206 (as illustrated in FIG. 28). The force generated by the compression of the sleeve 1206 provides for smooth and controlled downward movement of the collection cup 1200. As the sleeve 1206 compresses, the hollow needle 1202 engages the vacuum tube 1104 (i.e., pierces the membrane sealing the vacuum tube 1104) and the vacuum within the vacuum tube 1104 draws the specimen into the vacuum tube 1104 through the hollow needle 1202 (as illustrated in FIG. 29).

Figure 30:
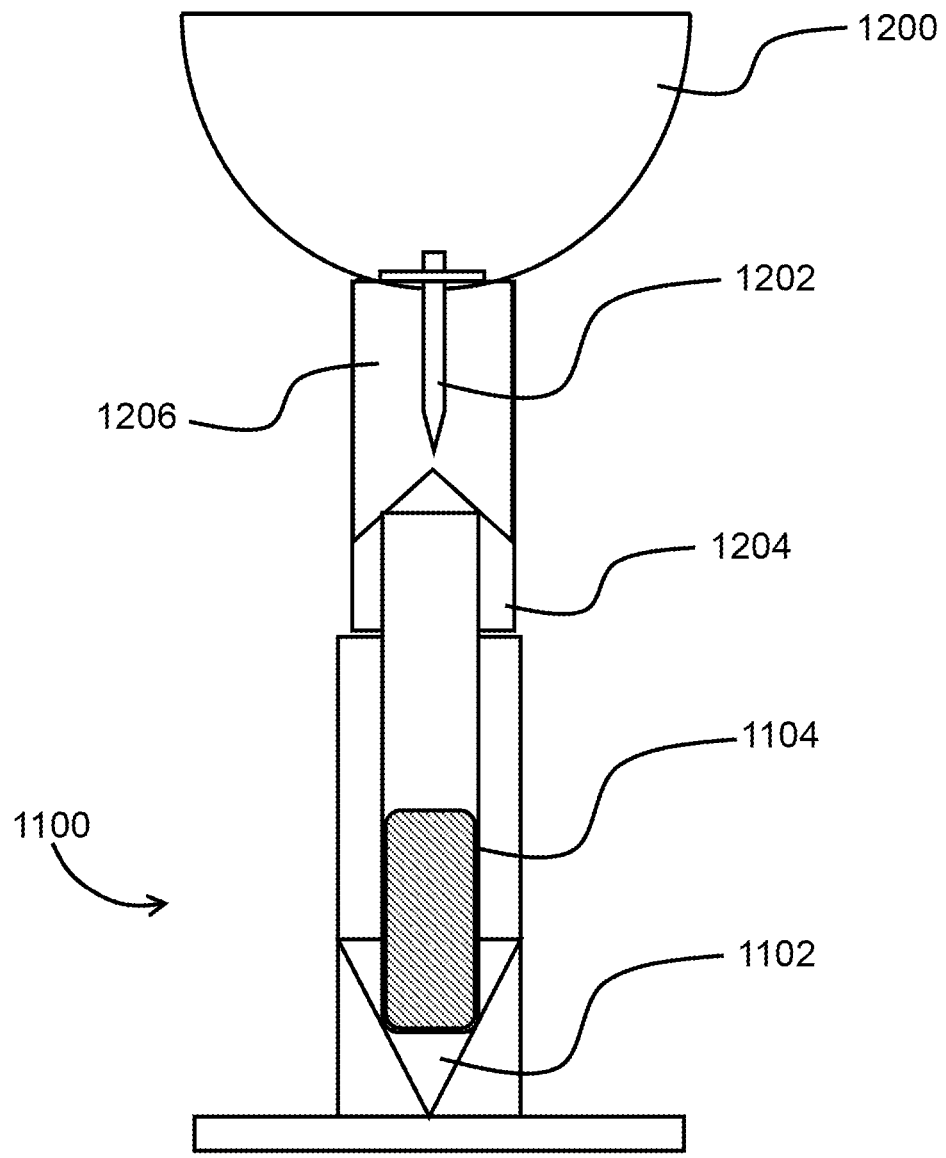
FIG. 30 is a schematic illustration of the exemplary collection cup of FIG. 24 in use with the exemplary base of FIG. 22.
Figure 31:
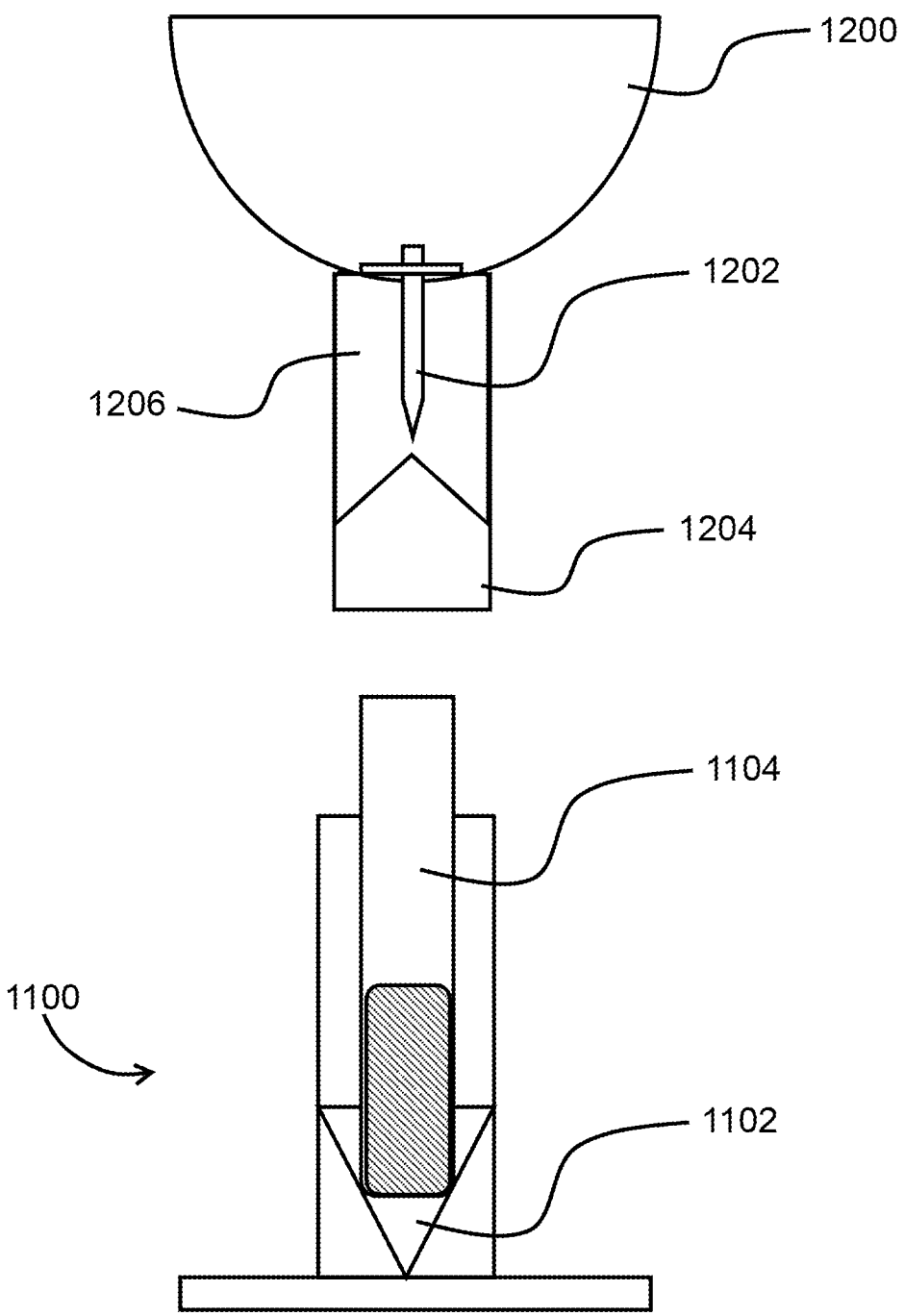
FIG. 31 is a schematic illustration of the exemplary collection cup of FIG. 24 in use with the exemplary base of FIG. 22.

Once the user or donor releases the downward pressure on the collection cup 1200, the resilient nature of the sleeve 1206 returns to its original shape and applies a force on the vacuum tube 1104. As illustrated in FIG. 30, such a force applied by the sleeve 1206 moves the collection cup 1200 upward, and the hollow needle 1202 is moved upward and withdrawn from the membrane sealing the vacuum tube 1104. Once the hollow needle 1202 and vacuum tube 1104 are disengaged, the collection cup 1200 can then be removed from the base 1100 (as illustrated in FIG. 31), and the user or donor can remove the vacuum tubes 1104 from the base 1100 and secure and package the vacuum tube 1104 for shipping or transport to a laboratory for testing. The sleeve 1206 once again covers the hollow needle 1202 to protect the user or donor when handling the oral fluid collection device. Once the vacuum tube 1104 is removed and secured, both the base 1100 and the collection cup 1200 can be discarded.

The foregoing description illustrates and describes the disclosure. Additionally, the disclosure shows and describes only the preferred embodiments but, it is to be understood that the preferred embodiments are capable of being formed in various other combinations, modifications, and environments and are capable of changes or modifications within the scope of the invention concepts as expressed herein, commensurate with the above teachings and/or the skill or knowledge of the relevant art. The embodiments described herein above are further intended to explain the best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended that the appended claims be construed to include alternative embodiments. It will be further understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. An assembly for collecting oral fluids, saliva, or sputum, comprising:
    a collection cup;
    at least one hollow needle positioned at least partially in the collection cup;
    a base engaged with the collection cup, the base comprising:
        a thin walled body; and
        a pedestal forming the bottom of the base positioned partially within the thin walled body and partially outside the thin walled body and arranged to move linearly relative to the thin walled body, the pedestal comprising:
            an upper surface;
            a lower surface; and
            a recessed section located between the upper surface and lower surface;
    at least one vacuum tube positioned at least partially within the thin walled body and in contact with the upper surface of the pedestal; and
    a removeable tab optionally positioned in the recessed section of the pedestal.

2. The assembly of claim 1, wherein when the removeable tab is positioned in the recessed section of the pedestal, the positional relationship between the at least one hollow needle and the at least one vacuum tube is static.

3. The assembly of claim 2, wherein when the removeable tab is removed from the recessed section of the pedestal, the at least one hollow needle and the at least one vacuum tube can move relative to each other.

4. The assembly of claim 1, wherein the assembly further comprises a vacuum tube holder positioned within the base and arranged to reversibly engage the one or more vacuum tubes.

5. The assembly of claim 1, further comprising at least one penetrable sleeves, each covering one of the at least one hollow needle.

6. The assembly of claim 1, further comprising a filter arranged to be positioned in an interior of the collection cup.

7. The assembly of claim 1, wherein:
    the assembly further comprises a cap;
    a hinge to rotationally secure the cap to the collection cup; and
    a protrusion and snap mechanism for closing an opening of the collection cup.

8. The assembly of claim 3, wherein as the at least one hollow needle and the at least one vacuum tube move closer to each other, the at least one hollow needle engages with the at least one vacuum tube.

9. The assembly of claim 1, wherein:
    the at least one hollow needle comprises a first hollow needle and a second hollow needle; and
    the at least one vacuum tubes comprise a first vacuum tube and a second vacuum tube.

10. The assembly of claim 9, further comprising:
    a first penetrable seal positioned to seal a top end of the first vacuum tube; and
    a second penetrable seal positioned to seal a top end of the second vacuum tube.

11. The assembly of claim 10, wherein when the removeable tab is positioned in the recessed section of the pedestal, the positional relationship between the first hollow needle and the first vacuum tube is static and the positional relationship between the second hollow needle and the second vacuum tube is static.

12. The assembly of claim 10, wherein when the removeable tab is removed from the recessed section of the pedestal, the first hollow needle and the first vacuum tube can move relative to each other and the second hollow needle and the second vacuum tube can move relative to each other.

13. The assembly of claim 12, wherein:
as the first hollow needle and the first vacuum tube move closer to each other, the first hollow needle penetrates the first penetrable seal; and
as the second hollow needle and the second vacuum tube move closer to each other, the second hollow needle penetrates the second penetrable seal.

14. The assembly of claim 9, wherein the assembly further comprises a vacuum tube holder positioned within the base and arranged to reversibly engage the first vacuum tube and the second vacuum tube.

15. The assembly of claim 9, further comprising a filter arranged to be positioned in an interior of the collection cup.

16. The assembly of claim 9, wherein:
the assembly further comprises a cap;
a hinge to rotationally secure the cap to the collection cup; and
a protrusion and snap mechanism for closing an opening of the collection cup.

17. The assembly of claim 9, wherein the base is reversibly secured to the collection cup.

18. The assembly of claim 9, further comprising a first penetrable sleeve covering the first hollow needle and a second penetrable sleeve covering the second hollow needle.

19. The assembly of claim 9 further comprising a resilient sleeve positioned in a bottom end of the collection cup.

20. The assembly of claim 19, wherein when the collection cup and the base are moved toward each other, the resilient sleeve compresses and applies a force resisting the collection cup and base moving toward each other.

21. The assembly of claim 20, wherein when the resilient sleeve is in an uncompressed state, the first hollow needle and a second hollow needle are positioned within the resilient material.

22. The assembly of claim 1, wherein the base is reversibly secured to the collection cup.

23. The assembly of claim 1 further comprising a resilient sleeve positioned in a bottom end of the collection cup.

24. The assembly of claim 23, wherein when the collection cup and the base are moved toward each other, the resilient sleeve compresses and applies a force resisting the collection cup and the base moving toward each other.

25. The assembly of claim 24, wherein when the resilient sleeve is in an uncompressed state, the first hollow needle and a second hollow needle are positioned within the resilient sleeve.

* * * * *